(12) United States Patent
Diller et al.

(10) Patent No.: US 12,011,465 B1
(45) Date of Patent: Jun. 18, 2024

(54) METHOD OF LUBRICATING BODILY TISSUE USING AN AMNION DERIVED THERAPEUTIC COMPOSITION

(71) Applicant: Amnio Technology LLC, Phoenix, AZ (US)

(72) Inventors: Robert B. Diller, Phoenix, AZ (US); Sarah Berglund, Mesa, AZ (US)

( * ) Notice: Subject to any disclaimer, the term of this patent is extended or adjusted under 35 U.S.C. 154(b) by 0 days.

(21) Appl. No.: 17/879,746

(22) Filed: Aug. 2, 2022

(51) Int. Cl.
| | | |
|---|---|---|
| *A61K 35/50* | (2015.01) | |
| *A61K 9/00* | (2006.01) | |
| *A61K 9/50* | (2006.01) | |
| *A61K 31/728* | (2006.01) | |
| *A61K 47/20* | (2006.01) | |

(52) U.S. Cl.
CPC ............ *A61K 35/50* (2013.01); *A61K 9/0024* (2013.01); *A61K 9/5084* (2013.01); *A61K 31/728* (2013.01); *A61K 47/20* (2013.01)

(58) Field of Classification Search
None
See application file for complete search history.

(56) References Cited

U.S. PATENT DOCUMENTS

| | | | | |
|---|---|---|---|---|
| 2008/0286378 | A1* | 11/2008 | Behrens | ............... A61K 35/50 424/528 |
| 2018/0000870 | A1* | 1/2018 | Britt | ....................... A61K 35/50 |
| 2018/0271915 | A1* | 9/2018 | Beaudry | ............. A61L 27/3604 |
| 2018/0311284 | A1* | 11/2018 | Harrell | ................. A61K 9/0048 |
| 2020/0353013 | A1* | 11/2020 | Young | ................. A61K 9/0019 |

* cited by examiner

*Primary Examiner* — Allison M Fox

(57) ABSTRACT

Acellular amnion derived therapeutic compositions are described having a number of various compositional embodiments. An acellular amnion derived therapeutic composition has essentially no live or active amniotic cells. The amniotic cells may be destroyed and the cells and cell debris may be removed from the acellular amnion derived therapeutic composition. An acellular amnion derived therapeutic composition may comprise micronized placental tissue particles, and/or amniotic fluid. An acellular amnion derived therapeutic composition may be a dispersion of micronized amniotic membrane combined with a fluid, such as plasma, saline, amniotic fluid, combinations thereof and the like. An acellular amnion derived therapeutic composition may be combined with a matrix component to form a composite. An acellular amnion derived therapeutic composition may be used in conjunction with a composition comprising viable cells, such as stem cells.

8 Claims, 24 Drawing Sheets

METHOD OF LUBRICATING BODILY TISSUE USING AN AMNION DERIVED THERAPEUTIC COMPOSITION

BACKGROUND OF THE INVENTION

Field of the Invention

The present invention relates to a method of lubricating bodily tissue, in particular joints, organs such as between the lungs and chest cavity, ligaments, muscle and tendons using a therapeutic compositions comprising amnion derived acellular material.

Background

Amnion derived materials are being used to treat a wide array of conditions such as to promote tissue healing. A widely known practice is to treat a treatment location with amniotic material comprising live amniotic cells, including amniotic stem cells in some case. This requires special handling, as the amniotic cells are fragile and will become inactive if not maintained in a proper condition, including temperature.

Amniotic material that is free of amniotic cells or that comprises no live or active amniotic cells may be a useful treatment composition and would require less stringent handling.

Pain and loss of mobility can result from friction between the tendon and tendon sheath. It is common to inject saline into the tendon to break up fibrotic adhesions and reduce tendon gliding resistance. While the saline aid in the break up of the fibrotic adhesions, it is not lubricious.

SUMMARY OF THE INVENTION

The invention is directed to a method of lubricating bodily tissue, in particular joints, organs, ligaments, muscle, connective tissue and tendons using a therapeutic compositions comprising amnion derived acellular material. During in utero development, amniotic fluid allows for the free motion of the fetus and provides mechanical cushioning and protection. Naturally occurring surfactants in the fluid are thought to provide lubrication that allows for both fetal and maternal movements while preventing wear or damage to the amniotic membrane. The factors which contribute to the surfactant nature of amniotic fluid are heterogeneous. Amniotic fluid contains the potent phospholipid surfactants also implicated in fetal lung maturation. In addition, amniotic fluid has been reported to contain an average of 1-2 μg/mL total hyaluronic acid with a high molecular weight (M>106) fraction of Hyaluronic Acid present late gestation (40 weeks). Although Hyaluronic Acid alone is a poor lubricant in vitro, Hyaluronic Acid is known to act at the cartilage-cartilage interface as a lubricant. Studies examining the gliding resistance of canine tendons in vitro demonstrated that removal of Hyaluronic Acid from the tendon surface resulted in increased friction between tendon and sheath.

A therapeutic composition comprising amnion derived material may be free of live, or viable cells including amniotic stem cells. An acellular amnion derived material includes at least one of the following: amniotic membrane, amniotic fluid, and/or the following derived from the amniotic membrane and/or amniotic fluid: proteins including growth factors and cytokines, extra-cellular proteins such as annexin, fibronectin, vitronectin, collagen and the like. An acellular amnion derived therapeutic composition may comprise amniotic stem cells that are not live or active. In some cases, the cell wall, also known as cell membrane, of an amniotic stem cell is ruptured and in other embodiments, essentially all complete and intact amniotic cells are removed from the acellular amnion derived therapeutic composition. In some embodiments, an amnion material, comprising growth factors and/or cytokines, is concentrated in a therapeutic composition, whereby the concentration is higher than in the received donor tissue or fluid. In other embodiments, a therapeutic composition, as described herein, comprises amnion materials, such as growth factors and/or cytokines, that are diluted or about the same concentrated as received from a donor. Additional materials including, but not limited to, carriers, diluents or a second therapeutic composition may be included with the amnion derived therapeutic composition. A second composition may comprise live or viable cells, including stem cells. Specific protein markers may be identified and measured to determine the concentration of the amnion derived components with a therapeutic composition.

An acellular amnion derived composition is a material derived from amnion material but contains essentially no live amniotic cells. In an exemplary embodiment, an amnion derived acellular composition comprises no live or active amniotic derived cells. In another embodiment, an acellular amnion derived therapeutic composition comprises essentially no intact amniotic derived cells. In yet another embodiment, an acellular amnion derived therapeutic composition is decellularized and comprises a reduced quantity of cells, such as no more than about five percent, no more than about three percent, no more than about two percent, or no more than about one percent of an original cell concentration. As described herein, during the micronizing of the amniotic membrane, some cells may be fractured, leaving cell fragments and essentially no intact cells. An acellular amnion derived composition may comprise live cells that are not derived from amnion however.

An acellular material, as used herein, is defined as a material having essentially no viable cells wherein no more than 1% of the total number of cells in the material are viable. In an exemplary embodiment, an acellular composition contains no viable cells. In an exemplary embodiment, an acellular composition is essentially cell free. Essentially cell free, as used herein, is defined as a composition that contains essentially no cells, wherein the cells have been removed or destroyed through cryo-fracturing, for example.

An acellular amnion derived therapeutic composition may comprise amniotic membrane and/or collagen to provide a scaffold for native cells to grow into. In an exemplary embodiment, an acellular amnion derived therapeutic composition comprises micronized particles of amniotic membrane. In still another embodiment, an acellular amnion derived therapeutic composition comprises a concentrated amniotic fluid. Amniotic stem cells may be present in an acellular amnion derived therapeutic composition, but they are not active and may be ruptured or otherwise physically compromised. Any of the amniotic derived materials described herein may be concentrated by removal of water or other fluids and may have a concentration that is at least about 10% higher, at least about 25% higher, at least about 50% higher, at least about 100% higher, at least about 200% higher, at least about 400% higher than a concentration as received in the donor material. As described herein, an amniotic derived composition may also be diluted or provided with components concentrations that are about the same as those as found in donor materials.

Amniotic cells including amniotic stem cells may be removed and/or made inactive. Amnion material, including amniotic membrane and amniotic fluid may be decellularized, made essentially acellular as defined herein, through any effective means including, but not limited to, centrifugation, lysis, enzymatic digestion, freezing, filtration, precipitation, flow sorting, sonication and through chemical treatment or any other process known in the art. Centrifugation may be used to reduce the number of cells within amniotic material or fluid. Amniotic fluid may be decellularized through centrifugation to reduce the number of cells down to about 750,000 or less intact cells per ml of amniotic fluid, about 450,000 or less intact cells per ml of amniotic fluid, about 300,000 or less intact cells per ml of amniotic fluid, or about 150,000 or less intact cells per ml of amniotic fluid. An as received amniotic fluid from a donor may comprise about 15 million cells per milliliter before centrifugation and therefore the cell concentration may be reduced to about five percent or less, about three percent or less, about two percent or less, or about one percent or less of the original cell concentration. Cells may be destroyed to produce cell fragments by the addition of chemicals that cause the cell wall of the amniotic stem cells to rupture, thereby making them inactive. The amniotic stem cells may be removed through sonication or filtration, for example. In other embodiments, the amniotic stem cells are made inactive but the cells or cell debris may be left in the amnion derived therapeutic composition.

In an exemplary embodiment, a therapeutic composition or a carrier fluid including an amniotic fluid is filtered down to remove any particles greater than 20 microns. This filtration step removes particles that may decrease the effectiveness of a lubricating composition as described herein. The amniotic fluid may be filtered and the combined components of a lubricating composition may be filtered to ensure larger particles are removed, such as greater than 20 microns. An initial gross filtration step may use a filter with an opening that are much larger than 20 microns, such as a calculi filter, to remove bodily tissue and other materials such as baby lanugo or hair. The lubricating fluid or amniotic fluid may also be centrifuged to remove solid particles from the fluid component, or amniotic fluid. Removing the larger particles allows the use of a smaller needle, such as a 25 to 30 gauge needle or smaller, for the injection and delivery of the lubricating composition. A smaller needle may allow more precise delivery to a treatment location and may cause less trauma and pain to the patient.

A lubricating composition may include a carrier fluid that may be or include dimethyl sulfoxide (DMSO) in a concentration that does change the physical characteristics to reduce the lubricating effectiveness. The concentration of DMSO may be about 3% or less, about 5% or less or even about 8% or less and any range between and include the DMSO values provided. A 10% solution of DMSO may be added to a lubricating composition or component and the composition may be further diluted. The physical properties of the lubricating composition, such as a lubricating fluid, including viscosity have been measured with the lubricating composition with and without DMSO and no significant changes have been detected or measured. The viscosity of the lubricating composition at 20° C. may be about 1.2 cP or more, about 1.4 cP or more, about 2.0 cP or more, about 2.5 cP or more about 3.0 cP or less and any range between and including the values provided, such as 1.4 cP to about 2.5 cP. The viscosity is measured according to United States Pharmacopia 912 (USP912). The DMSO may help to protect the proteins, such as from oxidation, in the lubricating composition during irradiating to sterilize the lubricating composition. Also, the DMSO is a cryoprotectant and may preserve the lubricating composition when frozen, such as below cryogenic temperatures. A lubricating composition may be irradiated to ensure that it is acellular as described herein and sterile to $10^{-6}$. It is desirable to have a concentration of proteins in the lubricating composition that is stable over a period of time after delivery to a treatment location and the DMSO may aid in retaining and maintaining protein concentrations. In addition, the lubricating composition may be frozen, including cryogenically frozen, before irradiation to aid in the reduction of oxidation of the proteins. Also, the final lubricating composition may be frozen for shipment to a treatment location, such as a hospital or clinic.

An acellular amnion derived therapeutic composition may be provided in a form for direct application to a treatment location, such as by topical application, spraying or use of an eye dropper, for example. In other embodiments, an acellular amnion derived therapeutic composition is provided with an applicator such as a sponge, gauze, or a biological applicator, such as an amniotic membrane or composite incorporating amniotic membrane. In still another embodiment, an acellular amnion derived therapeutic composition may be coated onto an applicator in specific locations to enhance healing, for example.

Any suitable treatment protocol may be used to administer an acellular amnion derived therapeutic composition to a treatment location. In one embodiment, an acellular amnion derived therapeutic composition is applied along with or subsequent to the application of an amniotic composition comprising live amniotic stem cells. For example, a therapeutic dose of live amniotic stem cells may be applied to a treatment location and a separate dose of acellular amnion derived therapeutic composition may be applied to the same treatment location. In addition, subsequent applications of an acellular amnion derived therapeutic composition may be applied to the treatment location to enhance the effectiveness of the treatment.

In another treatment protocol, cells, including in some embodiments, stem cells, derived from a secondary source may be applied to a treatment location and an acellular amnion derived therapeutic composition may also be applied to said treatment location. The secondary source may be from a patient and the stem cells may be derived from bone marrow, adipose tissue or a stromal vascular fraction (SWF}, for example. In still another embodiment, live stem cells derived from a secondary source, such as a stromal vascular fraction, may be added to an acellular amnion derived therapeutic composition to create an acellular amnion derived therapeutic composition comprising live non-amnion derived stem cells and an acellular amnion derived component, in this manner, the effectiveness of stem cells derived directly from the patient or a secondary source may be improved by the application of an acellular amnion derived therapeutic composition. The additional growth factors, cytokines and scaffolding materials applied to the treatment location along with the live stem cells may greatly increase the healing and regenerative effect. It is to be understood that the non-amnion active stem cells may be derived from any suitable location when applied with or combined with an acellular amnion derived therapeutic composition. An amnion derived composition, may be combined or mixed with a platelet rich plasma (PRP) and applied to a treatment location as described herein. For example, an amnion derived fluid composition comprising amniotic fluid and/or placental tissue particles may be mixed with PRP and used as a topical treatment composition, injectable treatment composition, intravenous treatment composition, oral treatment composition or used in an intraoperative procedure. In an exemplary embodiment, a therapeutic composition, as described herein, combined with PRP is injected into a joint such as the knee, injected into the scalp to promote hair growth, or used for cosmetic application, such as injections to reduce wrinkles.

In an exemplary embodiment, a SVF comprising live stem cells derived from the tissue of a patient, for example, may be combined with micronized amniotic membrane to form a therapeutic composition for said patient. The SVF may contain any of the following preadipocytes, mesenchymal stem cells (MSC), endothelial progenitor cells, T cells, B cells and mast cells as well as adipose tissue macrophages. In some embodiments, an acellular amnion derived therapeutic composition is doped with progenitor cells and the progenitor cells may be multipotent progenitor cells and/or pluripotent progenitor cells. Progenitor cells may be derived from a patient to be treated, such as from a stromal vascular fraction. Vascular fraction cells and/or progenitor cells may be included with a therapeutic composition to further improve effectiveness. Progenitor cells may be autologous or allogeneic.

An acellular amnion derived therapeutic composition may require cryopreservation as do compositions comprising viable amnion cells. In some embodiments, the acellular amnion derived therapeutic composition comprises no live or active stem cells and therefore, there is no requirement to preserve the composition to ensure viability of the stem cells upon thawing. An acellular amnion derived therapeutic composition may be able to be kept at room temperature or refrigerated for long periods of time prior to administering to a treatment location.

In one embodiment, a therapeutic composition, as described herein, comprises an acellular amniotic fluid that may be applied directly to a treatment location including topically, intravenously, intraoperatively, orally and the like. In addition, a therapeutic composition comprising an acellular amniotic fluid may be combined with a carrier fluid, such as saline, hydrogel, oils, and the like. Additional non-amniotic fluid derived cells may be added to an acellular amniotic fluid, including progenitor cells, stromal vascular fraction cells and the like. An exemplary process for preparing a therapeutic composition, includes decellularizing an amniotic fluid to produce an acellular amniotic fluid as described herein, and in some cases filtering the acellular amniotic fluid to remove debris. An acellular amniotic fluid may be concentrated to reduce the liquid content and to increase a solids concentration. Concentration may be performed through centrifugation, air drying, exposure to vacuum, exposure freeze-drying or any methods for concentration a fluid known in the art. The fluid content, as determined through TGA, for example, may be no more than about 75%, no more than about 50%, no more than about 25%, no more than about 10% and in some cases there may substantially no liquid having fluid content of no more than 2%. Subsequent to concentrating the acellular amniotic fluid, the acellular amniotic fluid may be rehydrated or combined with a carrier fluid to produce an acellular amniotic fluid having a concentration of components, such as proteins, cytokines, and growth factors that is greater, less than or substantially equal to the concentration of these components in an amniotic fluid received from a donor, or in an acellular amniotic fluid prepared as described herein, such as after decellularization and/or filtering.

In an exemplary embodiment, viable cells may be added to an acellular amniotic fluid to produce a therapeutic fluid component, as described herein. Cells may be derived from amnion materials including placental tissue, amniotic membrane and/or amniotic fluid, cells derived from a stromal vascular fraction and the like. In an exemplary embodiment, amnion derived cells that were removed from the amniotic fluid and/or amniotic membrane during the process of decellularization may be added back to the acellular amniotic fluid, such as during the rehydration step. In this way, a specific and controlled viable cell concentration may be produced, thereby producing a therapeutic composition with known concentrations of viable cells. A therapeutic composition comprising a known and controlled viable cell concentration may provide more effective treatment efficacy.

An acellular amniotic fluid or therapeutic fluid component, as described herein, may be combined with a support layer or matrix component, as described herein, including, but not limited to, polymer matrix material including a bioresorbable or fluoropolymer membrane, and/or an amniotic membrane. An acellular amniotic fluid or therapeutic fluid component may be coated onto or imbibed into a support layer to produce a therapeutic composite. An acellular amniotic fluid or therapeutic fluid component may comprise a plurality of micronized placental tissue, such as amniotic membrane particles which may be acellular, as described herein. The concentration of the micronized placental tissue particles may comprise viable amniotic membrane cells or additional viable cells may be added to the composition, including non-amnion derived viable cells, or viable cells that were removed from the amniotic fluid or membrane during prior processing.

In an exemplary embodiment, an acellular amniotic fluid is combined with a support, matrix component or amniotic membrane to produce a therapeutic membrane or composite and in a preferred embodiment, the acellular amniotic fluid is a concentrated acellular amniotic fluid having a higher concentration of proteins and growth factors than received in the donor material. In another exemplary embodiment, a therapeutic fluid component comprising acellular amniotic fluid and micronized amniotic membrane particles is combined with support or matrix component such as an amniotic membrane to produce a therapeutic membrane or therapeutic composite. The higher concentration of proteins and growth factors, for example, may provide greater treatment effectiveness. In still another exemplary embodiment, a therapeutic fluid component comprising an acellular amniotic fluid having viable cells added to the acellular amniotic fluid and micronized placental tissue particles. The additional viable cells added in this embodiment, such as stem cells may provide greater treatment effectiveness. This therapeutic fluid component may be combined with an amniotic membrane to produce a therapeutic composite. In particular, viable cells added to an acellular amniotic fluid may be cells removed from the amniotic fluid and/or membrane during the decellularization process as described herein. In this manner, the therapeutic composition is derived from a single donor and may comprise a therapeutic fluid component with a greater concentration of viable cells and/or proteins, for example, than the concentration of the donor material.

A therapeutic fluid component and/or a therapeutic composition comprising micronized placental tissue particles, may be combined with a support or matrix component, such as an amniotic membrane through methods of combining including coating, soaking, vacuum imbibing, electrophoresis, coating and drying with forced air to create a gradient of composition of components through the thickness of the amniotic membrane and the like. A therapeutic fluid or composition, as described herein may be coated only on one side of a support or amniotic membrane, or imbibed at least partially into the thickness of the amniotic membrane. In an exemplary embodiment, there is a gradient of concentration of proteins derived from the therapeutic fluid or therapeutic composition through the thickness of the amniotic membrane or support. In still another embodiment, viable cells are combined with a therapeutic fluid or composition before application or combining with a support or amniotic membrane. Again, the concentration of the viable cells may be uniform throughout the thickness or may have a gradient from one side to the opposing side, or through the thickness of the support. In an exemplary embodiment, the therapeutic composition or fluid is coated on one or both sides of the support, wherein substantially all of the therapeutic fluid or composition is configured on the surface, such a plurality of placental tissue particles.

In one embodiment an acellular amnion derived therapeutic composition, as described herein, comprises particles of micronized amniotic membrane and/or non-active or destroyed amniotic stem cells. In one embodiment, an acellular amnion derived therapeutic composition is a dispersion of micronized amniotic membrane combined with a fluid, such as plasma, saline, amniotic fluid, combinations thereof and the like. In one embodiment, the acellular amnion derived therapeutic composition consists essentially of a mixture of micronized placental tissue particles combined with amniotic fluid. In one embodiment, the acellular amnion derived therapeutic composition consists essentially of a mixture of micronized amniotic membrane particles, amniotic fluid and saline. An acellular amnion derived therapeutic composition may comprise a concentration of proteins including growth factors and cytokines that can be equal to, lower or higher than the concentration as received in the donor material.

The micronized amniotic membrane may comprise hydrated mammalian amniotic tissue having a percent hydration that is greater than zero, at least about 25%, at least about 50%, at least about 75% by weight or any range between the concentrations provided. Proteins can be more stable in concentrated compositions with lower percent hydrations. Amniotic membrane maintained in a hydrated state may provide for more regenerative properties. The particles in the therapeutic composition as described herein may consist essentially of amniotic membrane and be essentially free of chorion. The amnion layer may be removed from the chorion prior to processing. In one embodiment, the placental tissue particles consist essentially of amniotic membrane particles wherein the amnion layer consists of the epithelium, fibroblast layer and basement membrane compact layer. The placental tissue particles may consist essentially of any of these discrete amnion layers or any combination thereof. In an exemplary embodiment, the placental tissue particles consist essentially of epithelium wherein the concentration of the epithelium is about 70% or more, for example. The particles consisting essentially of epithelium may comprise stem cells and tissue that may substantially surround the stem cells. The amniotic membrane particles may be derived from dehydrated and/or decellularized amniotic tissue. An amniotic membrane may be cryo-fractured, such as with a blunt object to minimize shear and damage to tissue, thereby improving therapeutic effectiveness. Particles of amniotic membrane may have any suitable particle size, average particle size and particle size distribution. For example, the amniotic membrane derived particles, or micronized particles, may have a particle size, or an average particle size of no more than about 1000 µm, no more than about 100 µm, no more than about 75 µm, no more than about 50 µm, no more than about 25 µm, no more than about 10 µm and any range between and including the average particle sizes provided. The average particle size of the placental tissue particles can be determined through any suitable method, including image analysis, whereby a therapeutic composition is dried and imaged using a scanning electron micrograph (SEM). The amniotic membrane derived particles may have an irregular shape and, in some embodiments, may be planar having a first planar surface and a second planar surface. Cryo-fracturing of amniotic membrane with a blunt object provides particles with less shear and a more irregular shape than conventional cryo-milling, thereby providing a higher surface area and more effective therapeutic effect.

The concentration of particles, such as micronized amniotic membrane, in the therapeutic composition may be provided in any effective amount such as more than about 0.1%, more than about 0.5%, more than about 1%, more than about 10%, more than about 25%, more than about 50%, more than about 75%, or more than about 90% by weight of therapeutic composition and any range between and including the weight percentages listed. Likewise, the mass of particles, such as amniotic membrane particles, may be provided in a therapeutic composition in any effective amount, such as more than about 1 mg/ml, more than about 5 mg/ml, more than about 10 mg/ml, more than about 50 mg/ml, more than about 100 mg/ml, more than about 500 mg/ml, and any range between and including the mass concentrations provided. The particles in the therapeutic composition may comprise collagen, growth factors, stem cells, amniotic stem cells, mesenchymal stem cells, progenitor cells, red blood cells, white blood cells, proteins, fibroblasts, paratenacytes, keratinocytes and the like.

Additional fluids and agents may be added to the acellular amnion derived therapeutic composition including, but not limited to, Plasma Lyte-A, from Baxter Inc., saline and the like. An acellular amnion derived therapeutic composition, as described herein, may comprise anti-inflammatory nanoparticles and/or statins, and HMG-CoA reductase inhibitors to reduce inflation at a treatment location.

An acellular amnion derived therapeutic composition may comprise proteins, growth factors and cytokines derived from the placental tissue, such as amniotic membrane or fluid. Amnion derived protein may be identified in an acellular amnion derived therapeutic composition by a protein marker including, but not limited to, basic fibroblast growth factors (bFGF), bone morphogenetic protein 2 (bmp-2), bone morphogenic protein 4 (bmp4), bone morphogenetic protein 7 (bmp-7), bone morphogenic protein 9 (bmp-9), epidermal growth factor (EGF), insulin-like growth factor 1 (IGF-1), platelet-derived growth factor AA (PDGF-AA), platelet growth factor BB (PDGF-BB), platelet growth factor AB (PDGF-AB), transforming growth factor beta one (TGF-b1), and vascular endothelial growth factor (VEGF). Flow cytometry may be used to identify proteins markers such as, CD44, CD105, CD73, CD90, CD29, CD166, CD58 and other proteins found in amnion material. It is to be understood that any number of protein markers common to amniotic material may be identified in a composition to determine if the composition is amnion derived. Any other material derived from amnion material including the membrane and fluid may be included in an acellular amnion derived therapeutic composition, as described herein.

An acellular amnion derived therapeutic composition may be decellularized, made acellular, through any suitable means including, but not limited to, sterilization, lyophilizing, freezing, centrifuging, radiation exposure, chemical treatment and the like. In some embodiments, a therapeutic composition is acellular through a process of destroying or making inactive any live cells, such as amniotic stem cells. In another embodiment, essentially all cells, including amniotic stem cells, are removed from the therapeutic composition through filtration and/or centrifugation wherein no more than about five percent, no more than about three percent, no more than about two percent, or no more than about one percent of an original quantity of intact cells remains in a therapeutic composition, as described herein. In yet another embodiment, a therapeutic composition is acellular, comprising a plurality of dead cells, such as amniotic stem cells. Dead and/or destroyed cells may release proteins and growth factors into the therapeutic composition. An acellular therapeutic composition may comprise particles of amniotic membrane, such a cyrofractured or morselized amniotic membrane, as described herein. In another embodiment, an acellular amnion derived therapeutic composition consists of a fluid component that is essentially free of cells. For example, amniotic fluid may be centrifuged to substantially remove all the amniotic cells, including dead cells. In one embodiment, an acellular amnion derived therapeutic composition is sterilized and then stored at ambient temperature, or refrigerated to a temperature of greater than 0° C., frozen at a temperature of between about −80° C. to about 0° C., or is cryogenically stored at a temperature of less than about −80° C., prior to use.

An acellular amnion derived therapeutic composition may be dehydrated to reduce the moisture content to below 5%, and preferable being 2% and even more preferably to below 1%. A therapeutic composition, as described herein, including the a therapeutic fluid, placental tissue particles, support layer, amniotic membrane and combinations thereof may be dehydrated through freeze drying, air drying, application of heat and/or vacuum and the like.

Any of the acellular amnion derived therapeutic compositions described herein may be an injectable solution that will pass through any suitable needle, including 16 to 30 gauge needles or larger diameter needle. In some applications an acellular amnion derived therapeutic composition is provided through micro or nano-needles. An acellular amnion derived therapeutic composition may be provided to a patient transcatheter. In other embodiments, an acellular amnion derived therapeutic composition is provided in a thicker composition, such as a paste that may be applied topically. The viscosity of the injectable acellular amnion derived therapeutic composition may be no more than about 1 mPa sec, no more than about 500 mPa sec, no more than about 1000 mPa sec, no more than 20,000 mPa sec, no more than 50,000 mPa sec and any range between and including the viscosity values provided.

In other embodiments, an acellular amnion derived therapeutic composition may be provided for topical applications and the viscosity may be more than about 20 Pa sec, more than about 50 Pa sec, more than about 100 Pa sec, more than about 250 Pa sec and any range between and including the viscosity values provided.

The acellular amnion derived therapeutic composition described herein may be cryopreserved, whereby the temperature of the therapeutic composition is lowered to a temperature of no more than −65° C., and preferably lower than about −80° C. The rate of cooling may be controlled to reduce damage and maintain viability of the cells upon thawing.

An acellular amnion derived therapeutic composition, as described herein, may comprise an amniotic membrane to create an acellular therapeutic composite. A therapeutic composite comprising an amniotic membrane may be used in any suitable treatment method of use, as described herein. An amniotic membrane may be provided in a multilayered configuration or combined with any other suitable matrix component for a desired application. For example, an acellular therapeutic composite, as described herein, may comprise an amniotic membrane layer and a cover layer. A cover layer may be used to reduce the loss or wash-out of a fluid component from the acellular therapeutic composite. In another embodiment, the acellular therapeutic composite comprises an amniotic membrane and a support layer, such as a polymer matrix material including, but not limited to, a bioresorbable or fluoropolymer membrane. A support layer may have a tensile break strength that is much greater, such as two times or more, than that of an amniotic membrane layer in a matrix component. In still another embodiment, an acellular amnion derived therapeutic composite comprises one or more layers of amniotic membrane that are tensilized, whereby an amniotic membrane has been stretched in one or more directions to increase strength and/or area of the membrane. An amniotic membrane may be cross-linked, and a cross-linked amniotic membrane may be combined with a non-cross-linked amniotic membrane. Any suitable method as known in the art of cross-linking an amniotic membrane may be used including, but limited to, chemical treatment with glutaraldehyde, radiation and the like.

In another embodiment, a fluid component of an acellular amnion derived composite comprises amniotic membrane that has been micronized and dispersed in a fluid. In one embodiment, a fluid component is a dispersion of micronized amniotic membrane combined with a fluid, such as plasma, saline, amniotic fluid, combinations thereof and the like. In an exemplary embodiment, the fluid component and amniotic membrane are from a single donor. A fluid component, as described herein, may comprise anti-inflammatory nano-particles and/or statins, or HMG-CoA reductase inhibitors to reduce inflammation at a treatment location.

An acellular amnion derived therapeutic composite, as described herein, may be provided with the fluid component imbibed into, coated onto or otherwise applied to a matrix component. For example, an acellular amnion derived therapeutic composite comprising an amniotic membrane may be provided with a fluid component comprising micronized placental tissue particles dispersed in concentrated or diluted acellular amniotic fluid component. In an exemplary embodiment, the amniotic membrane and a fluid component are all from a single donor. In another exemplary embodiment, a therapeutic composite comprises an amniotic membrane layer configured for direct application to a treatment location, a cover layer of a bioresorbable material and a fluid component. A portion of a bioresorbable material or other matrix layer of the therapeutic composite may be porous to enable a portion of the fluid component to be retained therein. Any suitable number and type of matrix or support layers may be configured in a therapeutic composite, as described herein. In one embodiment, a fluid component may be vacuum imbibed into a matrix component; whereby a matrix component is submerged in a fluid component and vacuum is applied to remove air from the matrix component. This removal of air allows the fluid component to more substantially fill the voids and porosity of the matrix component.

A support layer may comprise any suitable type of material including, but not limited to, a bioresorbable material, a non-bioresorbable polymer material, such a polyether ether ketone (PEEK), or polytetrafluoroethylene (PTFE), fluorinated ethylene propylene (FEP), perfluoroalkoxy (PFA) and the like, or a metallic component, such as stainless steel, titanium, gold and the like. A support layer may be porous and/or permeable. A support layer may be a membrane having a microstructure of pores, or a film, net, screen, woven and the like. A support layer may be substantially non-permeable to fluid and may be hydrophobic or oleophobic on at least one side. In an exemplary embodiment, a support layer is expanded PTFE. In an exemplary embodiment, a support layer is a sheet of material having a first substantially planar surface, a second substantially planar surface and a thickness. An acellular amnion derived composition, may be provided with a stent, such as a self-expanding stent comprising Nitinol or a covered stent having a stent cover over at least a portion of the stent, such as an expanded fluoropolymer material. An acellular amnion derived composition may be coated directly onto a self-expanding stent, or an acellular amnion derived composition may be coupled to the stent. For example, an acellular amnion derived composition comprising an amnion membrane support layer may be attached to a self-expanding stent. Expanded PTFE is often used in covered stent applications and an acellular amnion derived composition may be coated onto or imbibed into the porosity, or pores of an expanded PTFE material.

Any of the acellular amnion derived therapeutic composition described herein may be used for a wide variety of treatment applications including, but not limited to, any organ, respiratory system, circulatory system, digestive system, central nervous system and the like. A therapeutic composition, as described herein, may be provided to any suitable treatment location of the body to induce an immunomodulatory and/or anti-inflammatory response. In another application, a therapeutic composition is introduced into a treatment location to reduce scaring and to promote healing, whereby the therapeutic composition aids in regeneration of new tissue. A therapeutic composition may be injected directly into an affected area or introduced intravenously.

An effective dose of an acellular therapeutic composition may be provided in one treatment or in several doses over a period of time. The specific treatment and dosing regime will depend on the type and severity of the condition to be treated.

In one embodiment, an acellular amnion derived therapeutic composition is injected into a specific treatment location through the use of a catheter, such as a steerable catheter and an injection implement configured on the introductory end of the catheter. For example, a catheter having an injection implement may be introduced to an artery, inserted to position the injection implement in proximity of the treatment location, whereby a dose of therapeutic composition is administered into the treatment location.

An acellular amnion derived therapeutic composition, as described herein, may be used in conjunction with any suitable matrix component including bioresorbable materials, synthetic polymer material, bone (cortical or cancellous) and membranes and the like. The therapeutic composition may be imbibed into, coated onto or otherwise combined with a matrix component for treatment. In an exemplary embodiment, a therapeutic composition is coated into a porous bioresorbable material and placed onto a treatment location.

An acellular amnion derived therapeutic composition may be a cosmetic composition and comprise one or more cosmetic components, as defined herein. An acellular amnion derived therapeutic composition may be a cosmetic composition that is configured for topical application, such as hydrogel, transdermal membrane, reservoir and microneedle type array, to the skin of a subject to reduce wrinkles, discolorations, improve appearance and the like. Cosmetic composition, as used herein, is defined as any substance or preparation intended to be placed in contact with the various external parts of the human body for the purpose to clean, perfume, change the appearance, protect, keep in good condition, or correct body odors. A cosmetic composition may comprise any suitable combination of cosmetic components including, but not limited to, water, hyaluronic acid, alcohols such as polyhydric, ethylene glycol, propylene glycol, tri-methylene glycol, butylene glycol, isoprene glycol and sorbitol, hydrocarbon polymers, silicone polymers, silicone emollient, silicone oligomer, natural oils derived from plants or animals, such as fruit or vegetable derived oils, mineral oil, wax, borax, acids including polylactic acids and surfactants.

An acellular amnion derived therapeutic composition may be made from amnion tissue and/or fluid from any suitable mammalian donor, including humans, horses, pigs, and the like. In addition, an acellular amnion derived therapeutic composition may be used to treat a treatment location of any suitable mammalian patient, including a human or horse for example.

The summary of the invention is provided as a general introduction to some of the embodiments of the invention, and is not intended to be limiting. Additional example embodiments including variations and alternative configurations of the invention are provided herein.

Any suitable therapeutic composition as described herein, and particularly a therapeutic composition comprising, acellular amniotic membrane particles and a carrier fluid comprising an acellular amniotic fluid; wherein the acellular amniotic membrane particles consist essentially of micronized amniotic membrane and wherein the therapeutic composition is essentially free of any viable amniotic membrane cells or viable amniotic fluid cells, may be used to treat a wide variety of treatment locations. A therapeutic composition may be applied topically to an external body treatment location or internally during an intraoperative procedure, and may be in the form or a cream, gel, lotion, or ointment, and/or may be configured into a patch or other delivery article. A therapeutic composition may be injected into a treatment location, through the use of a syringe with or without needles or in some cases a syringe coupled with a catheter into the arterial, venous, cerebrospinal systems. A therapeutic composition may be introduced intravenously, including transcatheter, intra-arterial or through cerebrospinal treating. A therapeutic composition may be introduced to a treatment location during an intraoperative procedure and the therapeutic composition may be applied topically, within a patch or other delivery article, or injected into a treatment location, for example. A therapeutic composition may be administered orally and may be in the form of a liquid, a capsule, or tablet.

A therapeutic composition, as described herein, may be applied topically to a treatment location, such as an external body treatment location. An external body treatment location is any portion or location of the body that can be treated through direct application of the therapeutic composition without any invasive measures, such as invasive surgery or the use of instruments, such as scopes or catheters. External body treatment locations include, but are not limited to, skin, hair or scalp, eyes, nose and mucous membranes, mouth and the oral cavity including the teeth and gums, and the ears. Topical treatment may involve direct application of the therapeutic composition to a treatment location or may involve spraying the therapeutic composition onto a treatment location, such as the mucous membranes in the nose or mouth or into or on vaginal tissue. In addition, the therapeutic composition may be in the form of a liquid, cream, gel, lotion or ointment. A cream is a semisolid dosage form containing one or more therapeutic compositions dissolved or dispersed in a suitable base. A gel is a semisolid system consisting of suspension made up of small inorganic particles or large organic molecules interpenetrated by a liquid. A lotion is used to categorize a topical suspensions, solutions and emulsions intended for application to the skin. An ointment is a semisolid preparation intended for external application to the skin or mucous membranes. In addition, a therapeutic composition, in any of the forms described herein, may be coupled with a delivery article, such as a patch or covering. For example, a therapeutic composition may be imbibed into a porous material that is configured as a patch or wound covering. A wound includes, but is not limited to, a break or cut in the skin or tissue, chronic wounds, diabetic wounds, venous leg ulcers, acute wounds, traumatic wounds, gangrene, surgical wounds, pressure ulcers, arterial ulcers, and neuropathic wounds.

An external body treatment location includes, skin, hair, hair follicle, or surrounding tissue, wound, such as a cut or break in the skin, cut, abrasion, ulcer, boil, ophthalmic lesion, pimple, a first, second or third degree burn, scar, keloid scar, eye, mouth, nose, mucous membrane and the like. A therapeutic composition may be used to treat a wide range of dermatological disorders, diseases, or conditions including, but not limited to, lupus, acne, blisters, psoriasis, rosacea, eczema, keloid, scars, shingles, skin aging, dry skin, wrinkles, alopecia, Steven-Johnson syndrome, and skin cancer. A therapeutic composition may be used to increase the rate of healing of an external body treatment location, such as a cut, wound, or abrasion. A therapeutic composition may be used to treat hair loss local or systemic, such as alopecia, hair loss immunomodulated or chemically induced or hormonally induced. A therapeutic composition may be used to treat atopic dermatitis of any etiology including immunomodulated, such as psoriasis, vitiligo or allergic response eczema (dyshidrotic), atopic from external irritant.

A therapeutic composition, as described herein, may be injected into a treatment location to promote healing and/or to reduce friction. A therapeutic composition may be configured into a syringe, for example, and the needle of the syringe may be inserted into treatment location for injection of the therapeutic composition, therein. A needle may pass into or through an external body portion, such as the skin, to inject the therapeutic composition internally or into an internal body portion, such as a muscle. In addition, during an intraoperative procedure, a therapeutic composition may be injected directly into an internal body portion, such as an organ.

A therapeutic composition may be injected into any portion of a joint, such as an articular joint including, but not limited to, a muscle in or around the joint, a ligament, a tendon, a meniscus, a bone within or proximal to the joint and the like. The therapeutic composition may reduce friction and also promote healing. A lubricating composition, a form of a therapeutic composition may be delivered to connective tissue that may include a ligament, cartilage, tendon, bones, dense regular tissue, dense irregular tissues and reticular connective tissue.

A therapeutic composition may be configured around an organ to reduce friction between the organ and other bodily tissue, such as muscle, or an enclosing bodily tissue, such as into the pericardium configured around the heart, or the into the pleura configured around the lungs.

A therapeutic composition may be injected into a treatment location associated with the musculoskeletal system, digestive system, respiratory system, urinary system, reproductive system, endocrine system, circulatory system, nervous system and the integumentary system. Areas for injection associated with the musculoskeletal system include, but are not limited to, joints, muscles, tendons, bones, and the like. Areas for injection associated with the digestive system include, but are not limited to, mouth, teeth, tongue, salivary gland, parotid gland, submandibular gland, sublingual gland, pharynx, esophagus, stomach, small intestine, duodenum, jejunum, Ileum, large intestine, liver, gallbladder, pancreas and the like. Areas for injection associated with the respiratory system include, but are not limited to, nasal cavity, pharynx, larynx, trachea, bronchi, lungs, diaphragm and the like. Areas for injection associated with the urinary system include, but are not limited to, kidneys, ureters, bladder, urethra and the like. Areas for injection associated with the reproductive system include, but are not limited to, ovaries, fallopian tubes, uterus, vagina, vulva, clitoris, placenta, testes, epididymis, vas deferens, seminal vesicles, prostate, bulbourethral glands, penis, scrotum and the like. Areas for injection associated with the endocrine system include, but are not limited to, pituitary gland, pineal gland, thyroid gland, parathyroid gland, adrenal gland, pancreas and the like. Areas for injection associated with the circulatory system include, but are not limited to, heart or any portion thereof, arteries, veins, capillaries, and the like. Areas for injection associated with the lymphatic system include, but are not limited to, lymphatic vessel, lymph node, bone marrow, thymus, spleen and the like. Areas for injection associated with the nervous system include, but are not limited to, brain or any portion thereof, cerebral hemispheres, diencephalon, the brainstem, midbrain, pons, medulla oblongata, cerebellum, spinal cord, ventricular system, choroid plexus, peripheral nervous system, nerves, cranial nerves, spinal nerves, sensory organs including the eye or any portion thereof, cornea, iris, ciliary body, lens, retina, ear or any portion thereof, outer ear, earlobe, eardrum, middle ear, ossicles, inner ear, cochlea, vestibule of the ear, semicircular canals, olfactory epthelium, tongue, taste buds, and the like. Areas for injection associated with the integumentary system include, but are not limited to, skin, subcutaneous tissue, mammary glands and the like.

A therapeutic composition may be injected into a treatment location to increase the rate of healing or to treat a disorder or disease. For example, a therapeutic composition may be injected into an incision to promote the rate of healing of the wound caused by the incision. In another example, a therapeutic composition may be injected into or around the base of the penis for the treatment of erectile dysfunction or peyronie's disease. In still another example, a therapeutic composition in injected into or around the spine to treat a degenerative disease or condition of the intervertebral disc, facets, or vertebral end plates, for example. In yet another embodiment, a therapeutic composition is injected into a bone to treat osteoporotic, traumatized with fracture bruising, non healing fracture, surgical repair of bone, to enhance the rate of bone healing. In still another example, a therapeutic composition is injected into or around the bladder to treat cystitis, urinary incontinence, overactive bladder, interstitial cystitis, and/or bladder cancer. In still another example, a therapeutic composition in injected into or around the liver to treat cirrhosis. In still another example, a therapeutic composition in injected into or around the brain to treat, seizures, trauma, Parkinson, autism, Alzheimer.

A therapeutic composition, as described herein, may be introduced intravenously, including into a patient's venous, arterial, cardiac or cerebrospinal system. Administering a therapeutic composition intravenously may be used to treat systemic conditions including, but not limited to, Neurologic origin: neuromuscular, such as Lou Gehrig's disease ALS, multiple sclerosis, Parkinsons, Dementia, Alzhiemers and the like. In addition, administering a therapeutic composition intravenously may be used to treat immunomodulated or autoimmune conditions, including, but not limited to, lupus erythematosus, sero (+) (−) arthritis, ulcerative colitis, chronic fatigue syndrome, Fibromyalgia. Administering a therapeutic composition intravenously may be used to treat cardiac related conditions including, but not limited to, myocardial infarction, atrial fibrillation, congestive heart failure, endocarditis, cardiomyopathy and the like. Administering a therapeutic composition intravenously may be used to treat urologic disorders or disease such as interstitial cystitis, erectile dysfunction, urinary incontinence, urinary tract infection, renal failure. Administering a therapeutic composition intravenously may be used to treat kidney disorder or disease including, but not limited to, chronic kidney disease based on measured or estimated GFR (Glomerular Filtration Rate). Administering a therapeutic composition intravenously may be used to treat pulmonary disorder or disease including, but not limited to asthma, chronic obstructive pulmonary disease (COPD), idiophathic pulmonary fibrosis, alveolitis, chronic parenchymal lung disease, pleural lung disease, trans-bronchial parenchymal disease or post-operative lung recovery and scaring. Administering a therapeutic composition intravenously may be used to treat disorders or disease of the bladder, liver, heart, lungs, brain blood, neuromuscular and the like. A therapeutic composition, as described herein, may be introduced intravenously through introduction into the pulmonary artery, a central venous catheter, a trans-bronchial catheter, and the like.

A therapeutic composition, as described herein, may be introduced intraoperatively, wherein the therapeutic composition in administered to internal body treatment location during an intraoperative procedure. For example, during an operation, a patient's internal organs may be exposed through an incision and a therapeutic composition may be applied to an organ topically, or through direct injection into the organ. The needle of the syringe may be inserted directly into any internal body treatment location including an incision, an organ, or intestine, and the like. In another embodiment, a therapeutic composition is applied topically to an internal body treatment location or configured in a patch or delivery article and applied directly to an internal body treatment location.

A therapeutic composition, as described herein, may be administered orally and may be in the form of a liquid or gel, capsule or tablet. A patient may be directed to take an effective amount of therapeutic composition orally to treat a gastrointestinal disorder or disease, a stomach disorder or disease, a stomach ulcer, crohn's disease, gastrointestinal polyps and the like.

A therapeutic composition, as described herein, may be configured as a suppository and administered anally to treat, hemorrhoids and the like. A therapeutic composition may be applied topically or through injection to treat hemorrhoids as well.

A therapeutic composition, as described herein, may be administered in any effective way described herein to treat neuromuscular disease or disorders including, but not limited to, multiple sclerosis, myasthenia gravis, amyotrophic lateral sclerosis, spinal muscular atrophy and muscular dystrophy.

A therapeutic composition, as described herein, may be administered in any effective way described herein to treat heart disease or disorders including, but not limited to, coronary artery disease, abnormal heart rhythms, congenital heart disease, cardiomyopathies, pericarditis and arterial fibrillation.

A therapeutic composition, or lubricating composition, as described herein may be introduced into body tissue, such as being injected into a tendon, to reduce friction. Efficient and optimal tendon function depends greatly on the ability of the tendon to glide freely, with minimal resistance. The tribology of normal tendon motion has demonstrated that gliding resistance is dependent on three factors, (1) the coefficient of friction at the interface, (2) the load on the tendon, and (3) the angle of the arc the tendon makes with the pulley. 1 In healthy tendon tissue, a natural lubrication system is in place that reduces the local coefficient of friction by bathing the tendon in hyaluronic acid, phospholipids and proteoglycans—either from synovial fluid or bound at varying anatomical locations along the tendon surface. 2 Factors known to increase gliding resistance include surface tears, tendon grafts (potentially from either methods and materials, or both), and the formation of surface adhesions post-repair or healing.

A therapeutic composition, as described herein, including an acellular amnion derived therapeutic composition, provides naturally occurring surfactants, derived exclusively from amniotic fluid, to supplement the natural lubrication of the tendon and reduce tendon gliding resistance when tendon gliding is impaired by one or more of the factors listed above. A therapeutic composition may be used as the injection fluid during the minimally invasive lysis of intraarticular adhesions by joint manipulation, a procedure known as brisement; leaving behind a lubricated local environment post-procedure. A therapeutic composition may also be placed by an experienced provider to supplement lubrication when minor injury is suspected or by an experienced orthopedic surgeon to bathe sutures post-tendon repair or trimming. The naturally occurring surfactants supplied by a therapeutic composition to minimize the coefficient of friction at the tendon gliding surface.

An amnion derived therapeutic composition for lubricious application may include a carrier fluid or other components such as a cryopreservation component, or solvent. The concentration of an amnion derived component in the amnion derived therapeutic composition may be 10% or more, 25% or more, 50% or more, 75% or more, or even 90% or more or 100% amnion derived material. As shown in Table 1, below an amnion derived therapeutic composition contains 50% filtered acellular amniotic fluid and 50% cryopreservation material, that may contain dimethyl sulfoxide (DMSO) in an effective concentration, as described herein, available from Biolife Solutions, Bothell, WA. The therapeutic composition, and particularly a lubricating composition may contain no more than about 70% of the carrier fluid by volume or weight of the lubricating composition, or no more than about 60%, no more than about 50%, no more than about 30% by volume or weight and any range between and including the percentages provided. The higher the concentration of the carrier fluid, the less proteins which may reduce the effectiveness and longevity of the effectiveness of the lubricating composition or fluid.

TABLE 1

| Component | Purpose | Final Product Ratio (v/v) | Volume per mL |
| --- | --- | --- | --- |
| Filtered Amniotic Fluid | Naturally occurring source of HA and phospholipid surfactants | 1 | 500 µl |
| Carrier Fluid | Solvent | 1 | 500 µl |

The summary of the invention is provided as a general introduction to some of the embodiments of the invention, and is not intended to be limiting. Additional example embodiments including variations and alternative configurations of the invention are provided herein.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

Figure 1A:
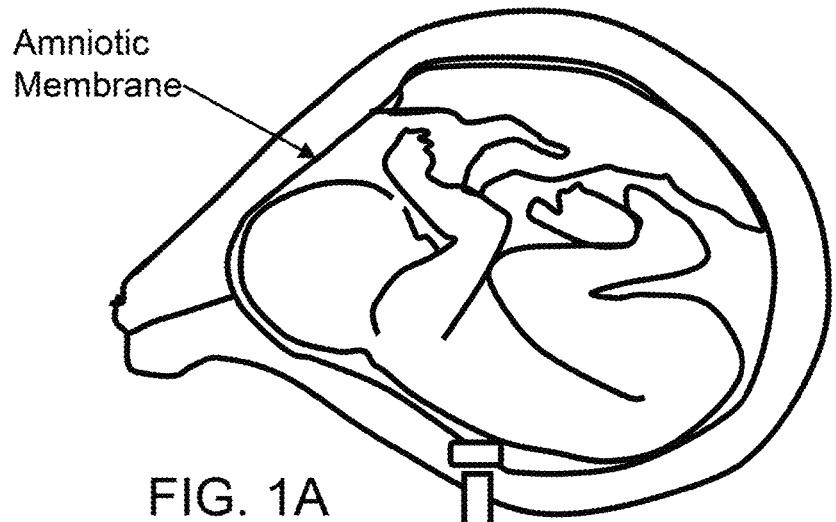
FIG. 1A shows a cross-sectional diagram of amniotic membrane surrounding a fetus in utero.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

DETAILED DESCRIPTION OF THE ILLUSTRATIVE EMBODIMENTS

Certain exemplary embodiments of the present invention are described herein and illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Figure 1B:
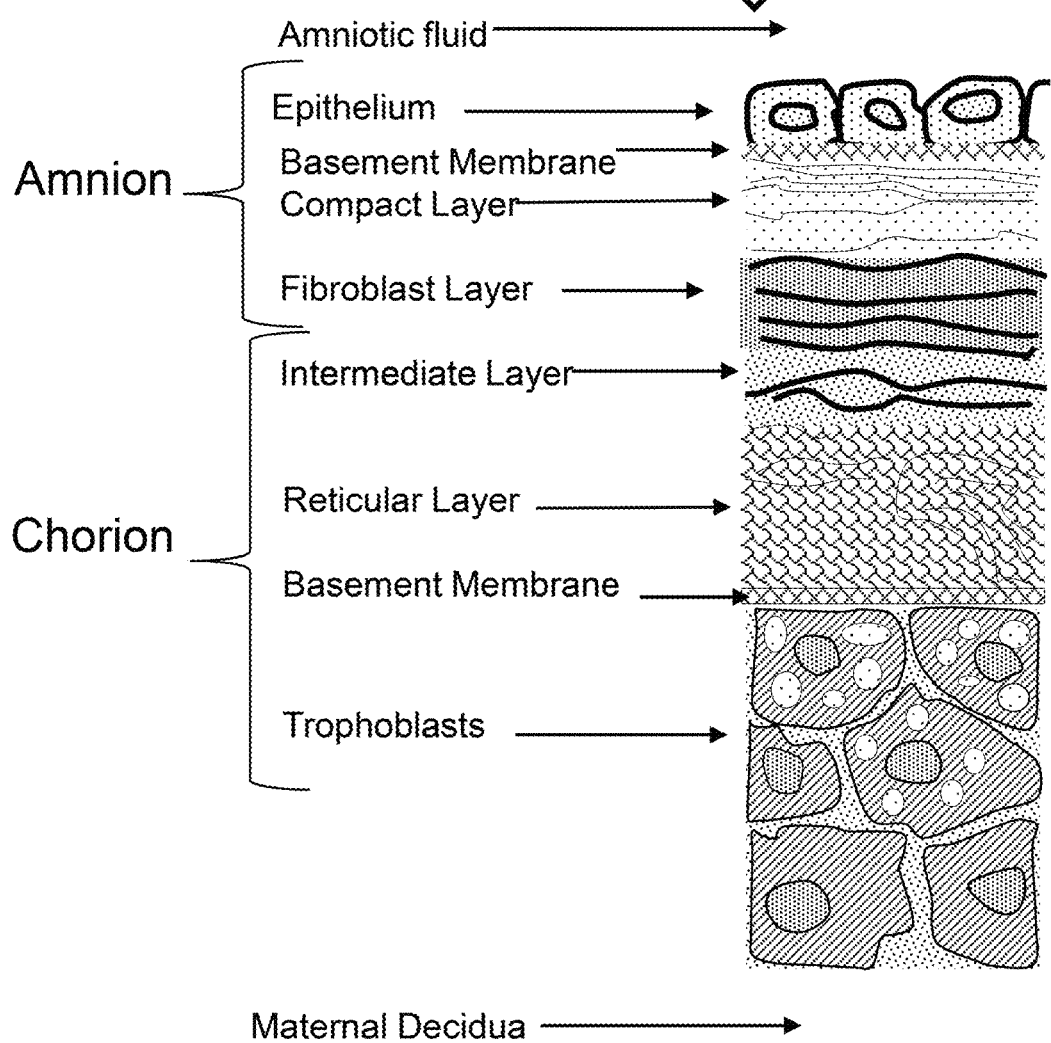
FIG. 1B shows a cross-sectional diagram of the layers of the amnion and chorion.

As shown in FIG. 1A the amniotic membrane surrounds a fetus in utero. As shown in FIG. 1B, the amniotic membrane comprises an amnion portion and a chorion portion. As described herein, the amnion portion may be separated from the chorion. In an exemplary embodiment, the epithelium, or inner most layer of the amniotic membrane, is removed and used to produce particles for the acellular amnion derived therapeutic composition, as described herein. The particles may consist essentially of the epithelium, consist essentially of the epithelium and base membrane, consist essentially of the epithelium, base membrane and compact layer, or consist essentially of epithelium, base membrane, compact layer, and fibroblast layer.

Figure 2A:
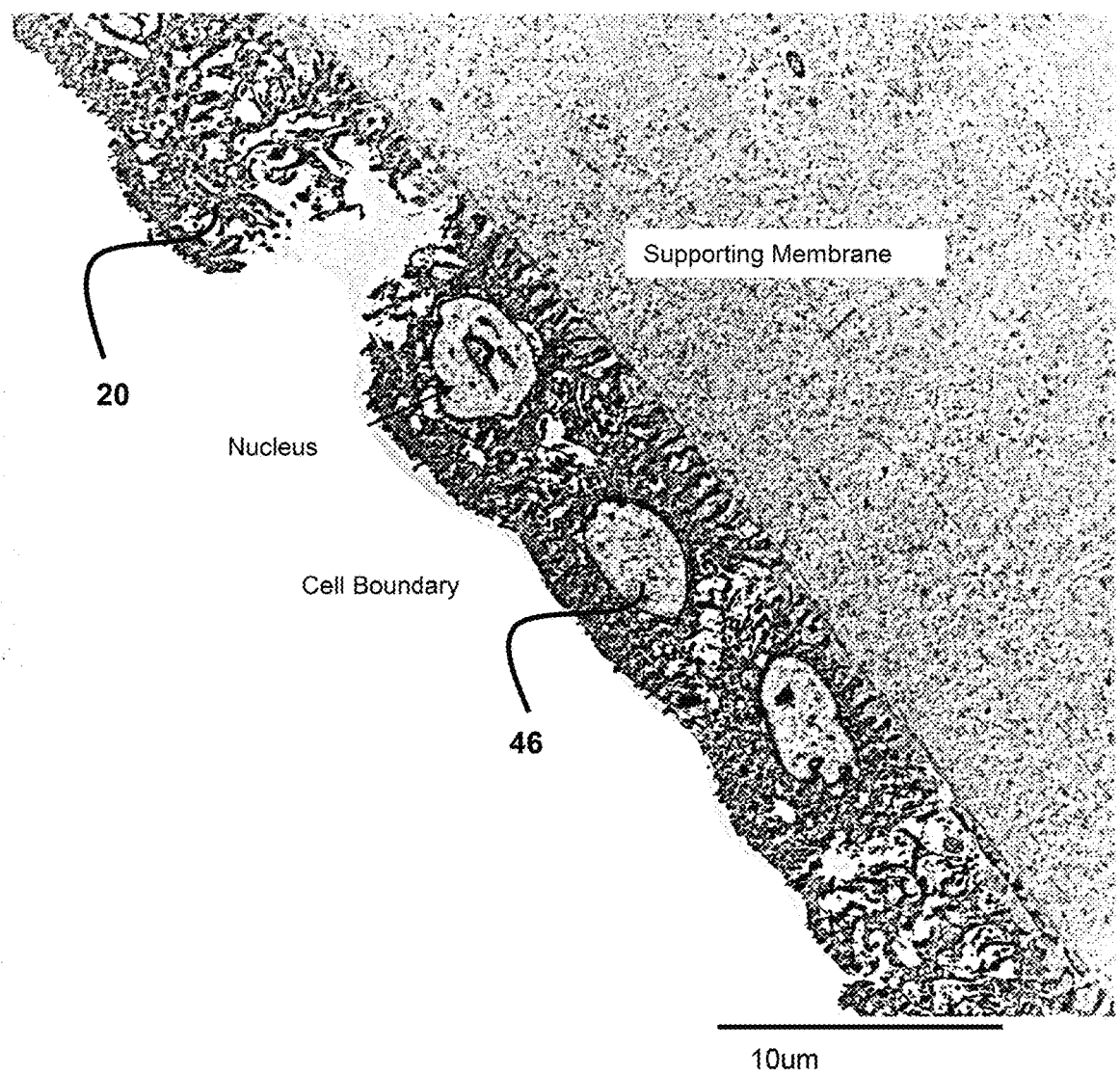
FIG. 2A shows a transmission electron micrograph (TEM) of the epithelium layer of the amniotic membrane having a single layer of amniotic cells. The TEM was taken at 2500× magnification.
Figure 2B:
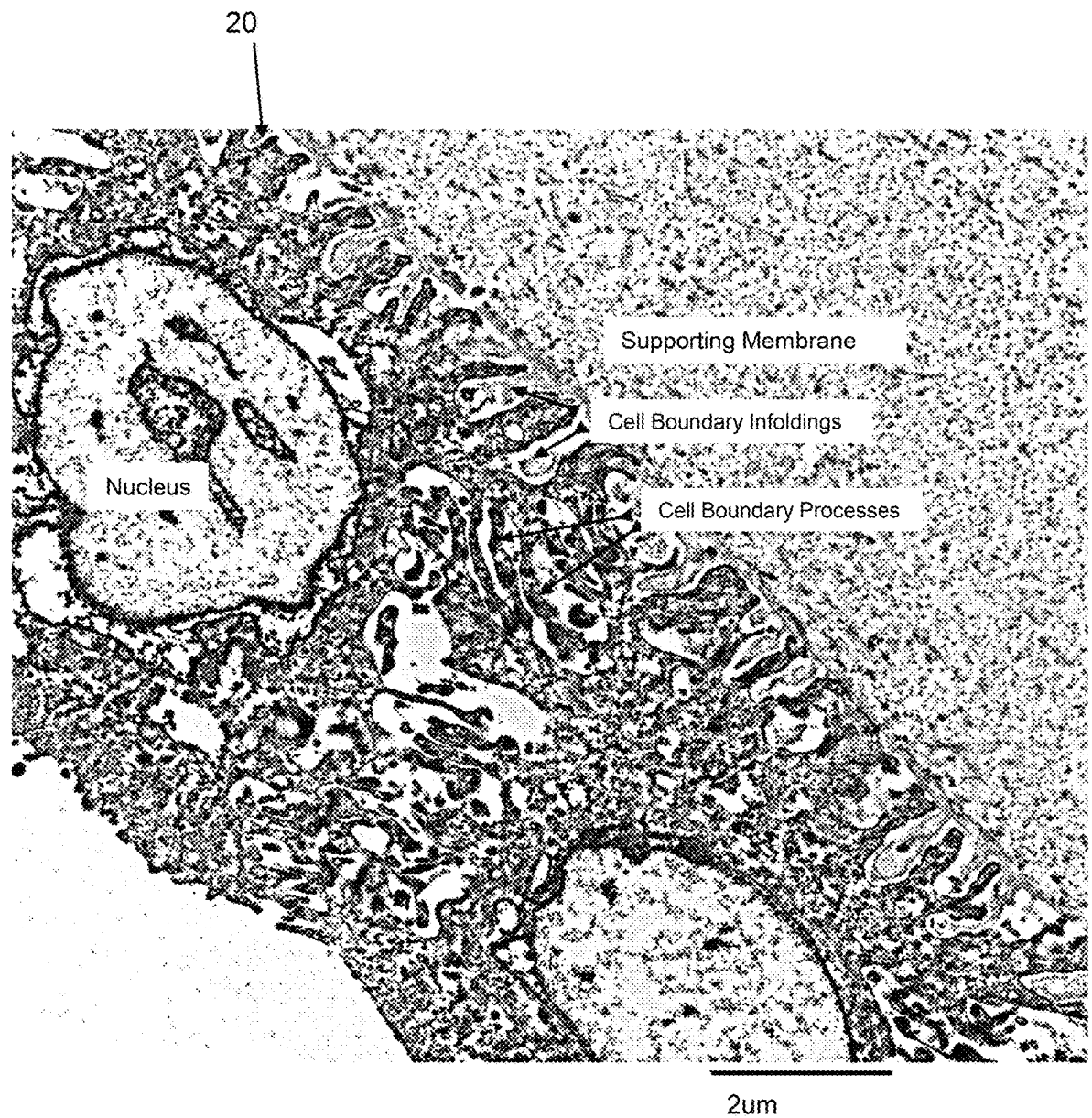
FIG. 2B shows a TEM of the epithelium layer of the amniotic membrane having a single layer of amniotic cells. The TEM was taken at 8200× magnification.

As shown in FIGS. 2A and 2B, the epithelium layer of the amniotic membrane 20 has a single layer of amniotic stem cells 46. The tissue around the amniotic stem cells may protect and enhance the viability of these stem cells when the epithelium is cryo-fractured to produce particles for the therapeutic composition.

Figure 3A:
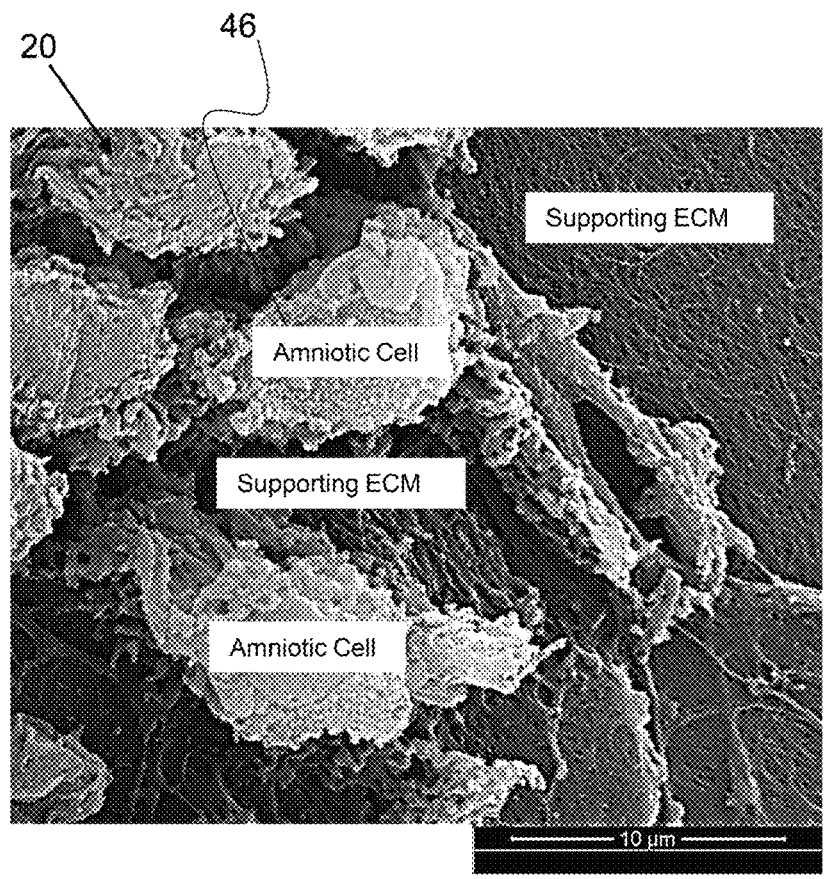
FIG. 3A is a scanning electron micrograph (SEM) of an amniotic membrane having amniotic cells.

As shown in FIG. 3A, an amniotic membrane 20 comprises a plurality of amniotic stem cells 46.

Figure 3B:
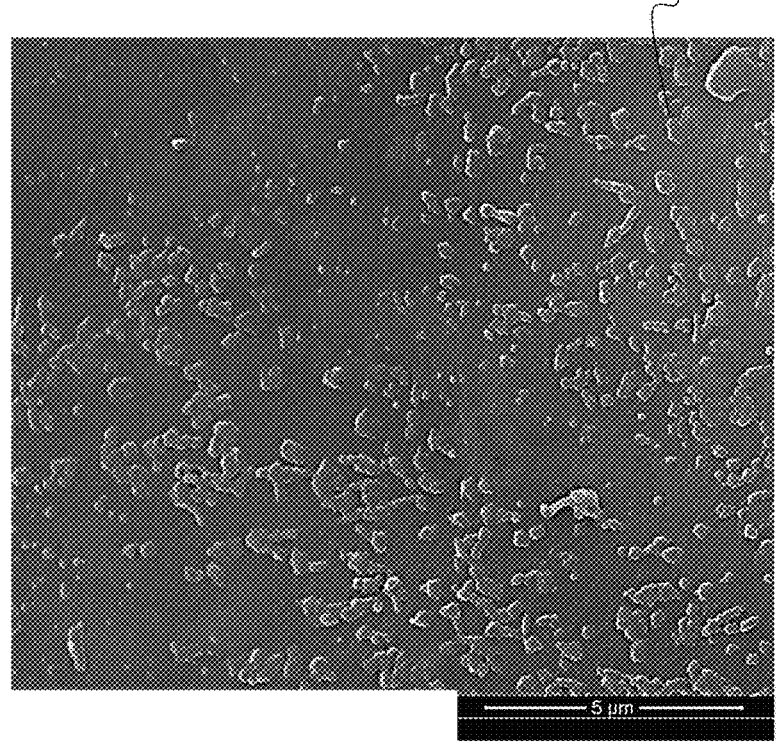
FIG. 3B is a SEM of cryo-fractured amniotic membrane particles.

As shown in FIG. 3B, particles of cryo-fractured amniotic membrane particles 40 are on the order of 0.2 to 0.5 µm in size. The average particle size shown is less than 2 µm. There are no particles shown that are larger than 2 µm and substantially all of the particles are less than 1 µm in size. The SEM shows that the micronized amniotic membrane particles are irregularly shaped. As shown, some of the particles have a planar surface.

Figure 4:
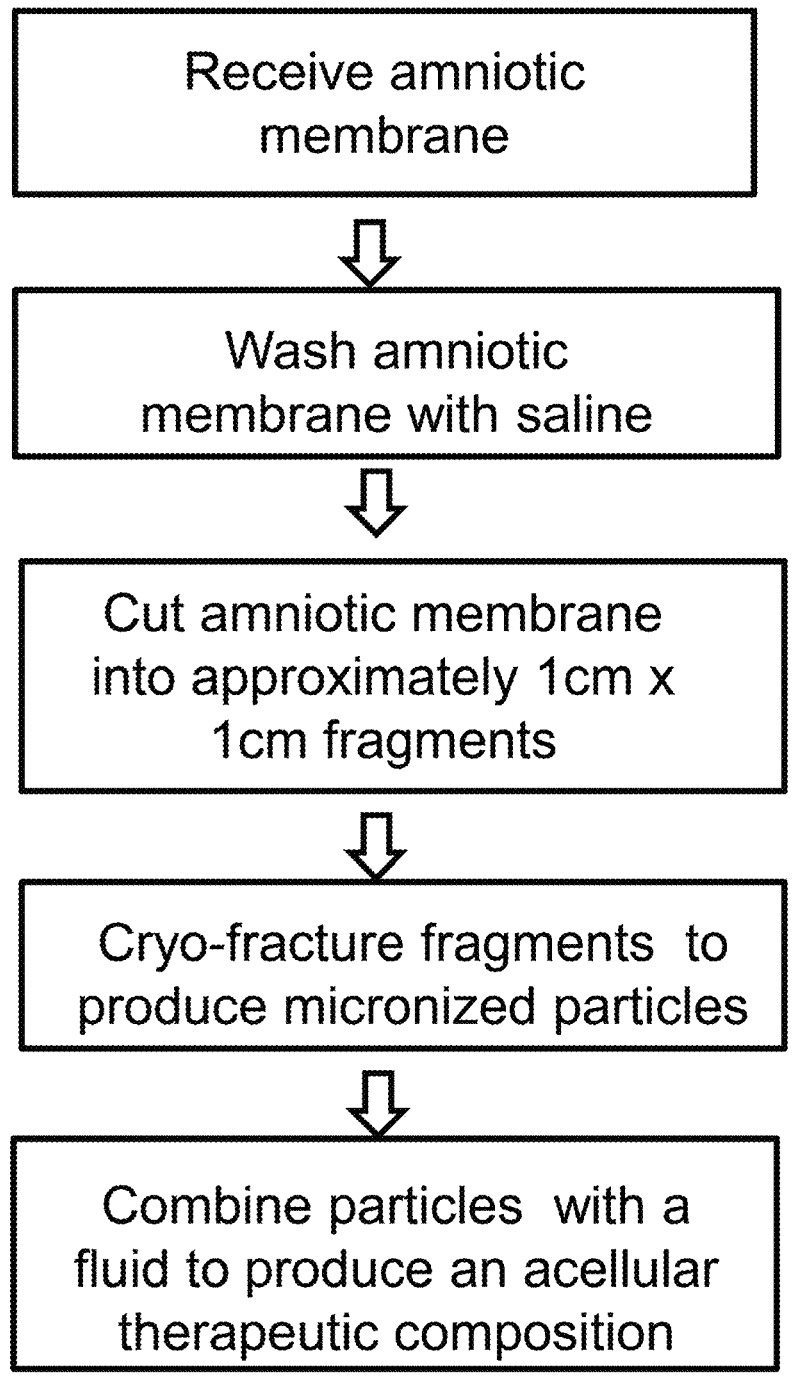
FIG. 4 shows a diagram of a process to produce an acellular amnion derived therapeutic composition comprising micronized amniotic membrane particles.

As shown in FIG. 4, a process to produce an acellular amnion derived therapeutic composition, as described herein, comprises the steps of cryo-fracturing amniotic membrane fragments to produce micronized amniotic membrane particles. As described, the amniotic membrane fragments may be cryo-fractured with a blunt object, such as a bar, that reduces shear and damage to the particles. In a preferred embodiment, the fragments are cryo-fractured with an object having substantially no sharp edges. The micronized particles are combined with any suitable carrier fluid to produce an acellular amnion derived therapeutic composition. In an exemplary embodiment, the micronized particles are dispersed in a fluid comprising amniotic fluid. The cells in the amniotic membrane may be destroyed prior to or after the process shown in FIG. 4, or between any of the steps.

Figure 5:
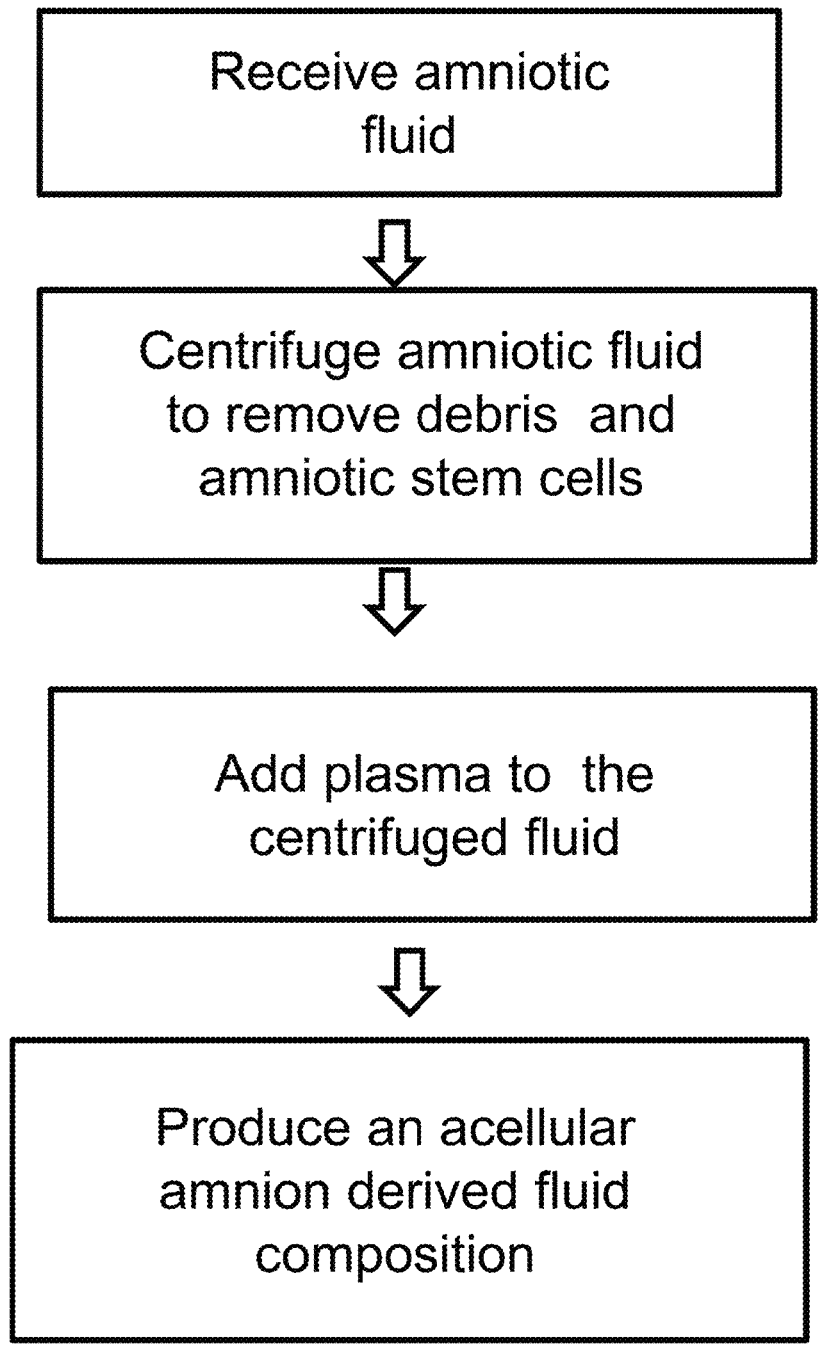
FIG. 5 shows a diagram of a process to produce an acellular amnion derived therapeutic composition comprising a concentrated amniotic fluid.

As shown in FIG. 5, a process to produce an acellular amnion derived therapeutic composition, as described herein, comprises the steps of concentrating an amniotic fluid component comprising Plasma Lyte-A, available from Baxter Inc. An amniotic fluid may be processed in any suitable way to concentrate the amniotic fluid and components therein. For example, an amniotic fluid may be heated or allowed to evaporate, with or without vacuum, to concentrate the amniotic fluid. The cells in the amniotic fluid may be destroyed prior to or after the process shown in FIG. 5, or between any of the steps.

Figure 6:
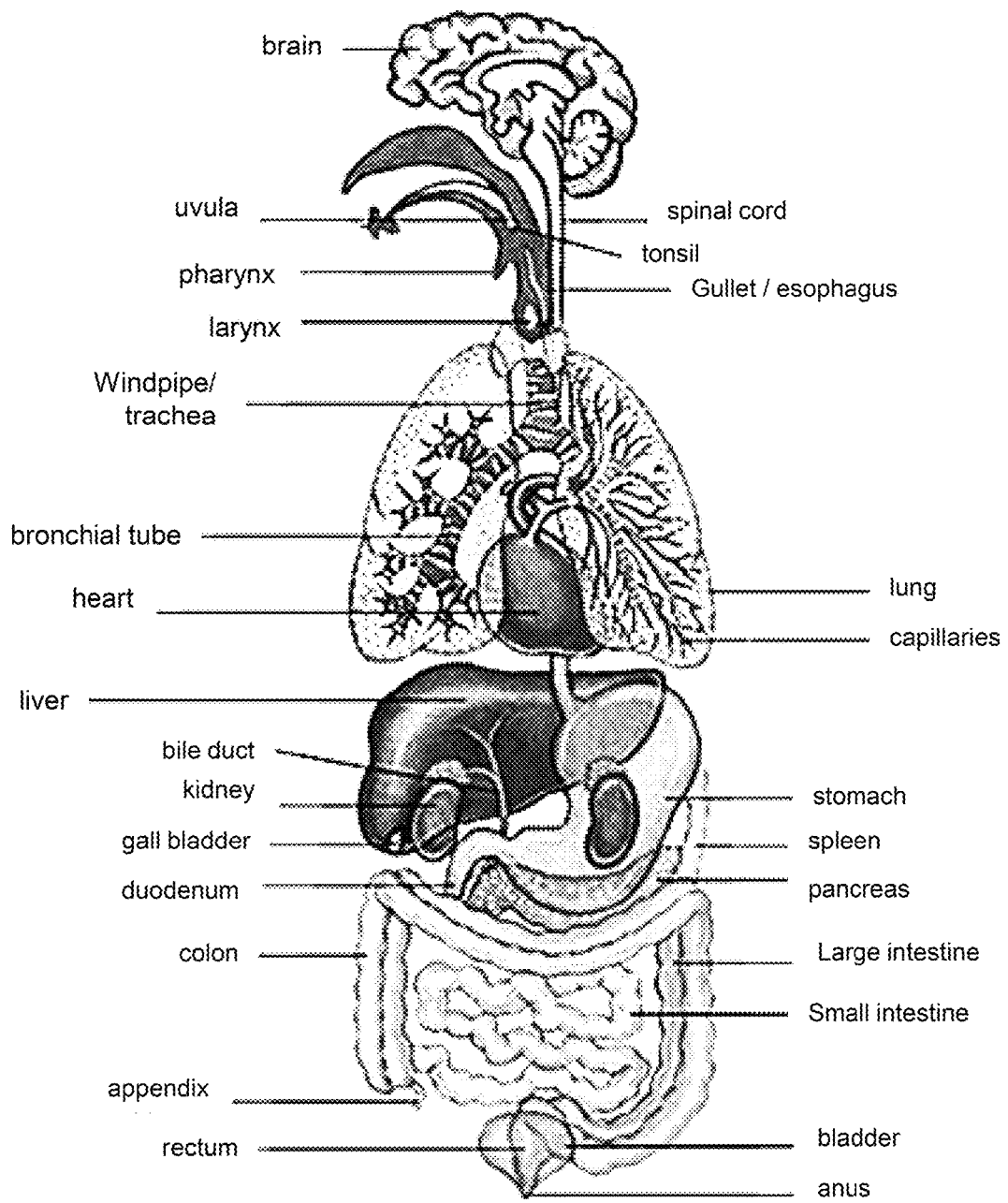
FIG. 6 shows a diagram of the anatomy and various organs within the body.

FIG. 6 shows a diagram of the anatomy and various organs within the body that may be treated with an acellular amnion derived therapeutic composition as described herein. An acellular amnion derived therapeutic composition, as described herein, may be introduced into any anatomy shown in FIG. 6 by direct injection, topical application, or transcatheter.

Figure 7:
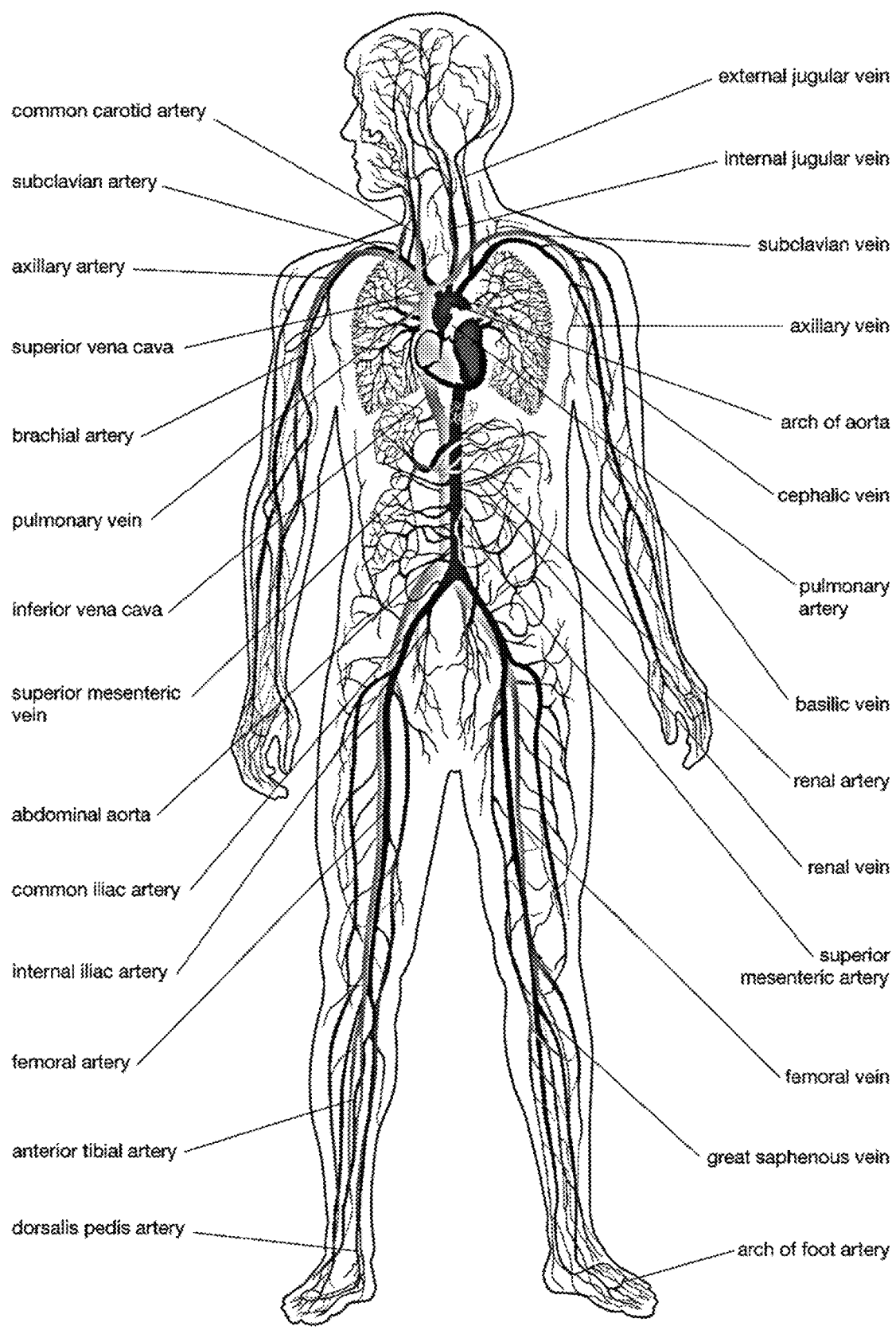
FIG. 7 shows a diagram of the circulatory system.

FIG. 7 shows a diagram of the circulatory system where an acellular amnion derived therapeutic composition may be introduced into the body through injection or transcatheter.

Figure 8:
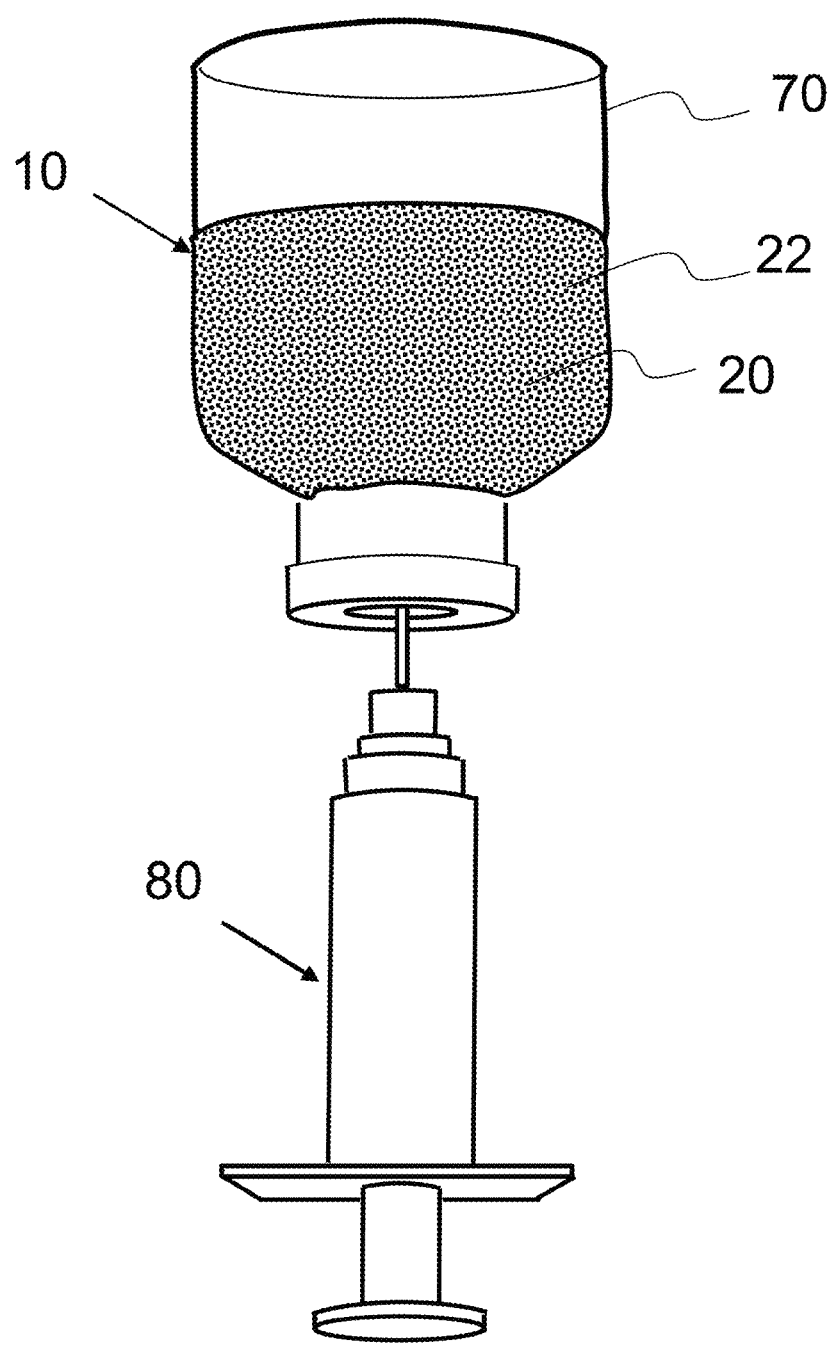
FIG. 8 shows an exemplary acellular amnion derived therapeutic composition being drawn from an enclosure by a needle.

FIG. 8 shows an exemplary acellular amnion derived therapeutic composition 10 being drawn from an enclosure 70 by a syringe 80. The acellular amnion derived therapeutic composition comprises micronized particles 22 of amniotic membrane 20. The needle may be any suitable size, however in a preferred embodiment the needle is no larger than a 20 gauge needle.

Figure 9:
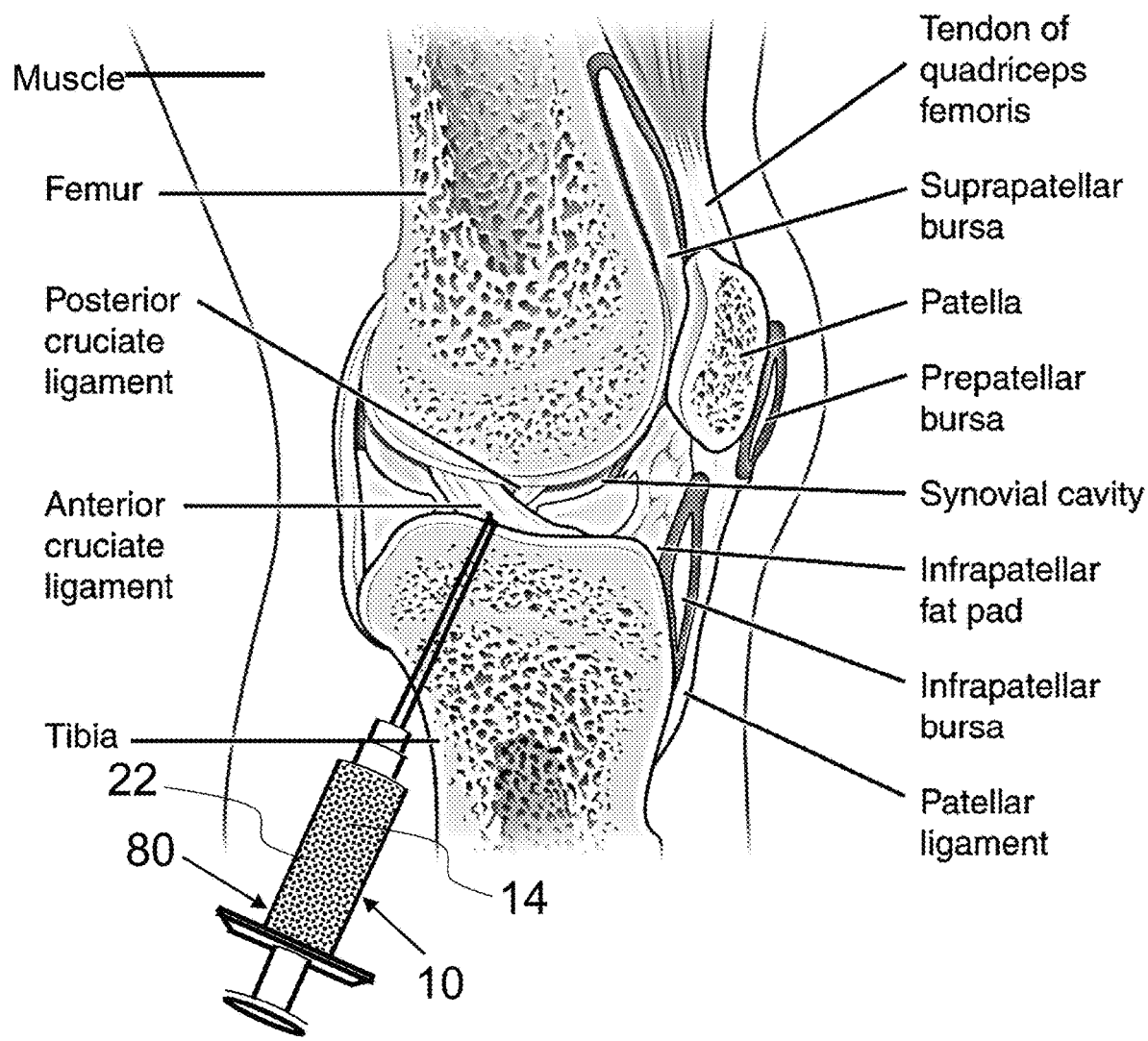
FIG. 9 shows a knee joint and a syringe injecting an acellular amnion derived therapeutic composition into the knee joint.

As shown in FIG. 9, a syringe 80 is injecting an acellular amnion derived therapeutic composition 10 comprising micronized particles 22 of amniotic membrane 20 dispersed in a fluid component 14 into the knee joint.

Figure 10:
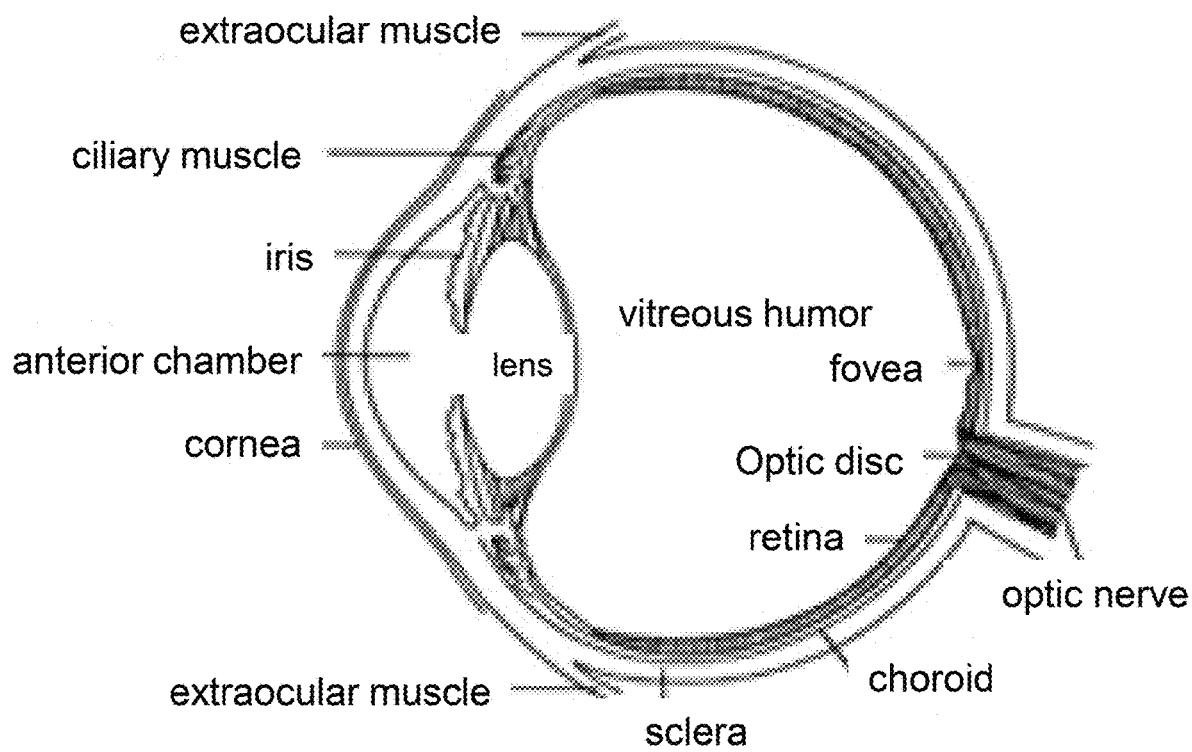
FIG. 10 shows a cross-sectional diagram of an eye.

FIG. 10 shows a cross-sectional diagram of an eye and some of the treatment locations for an acellular amnion derived therapeutic composition, as described herein. For example, an acellular amnion derived therapeutic composition, as described herein, may be applied topically and/or injected into the iris, anterior chamber, lens, vitreous humor, cilliary muscle, cornea, extraocular muscle, sclera, choroid, retina and the like.

Figure 11:
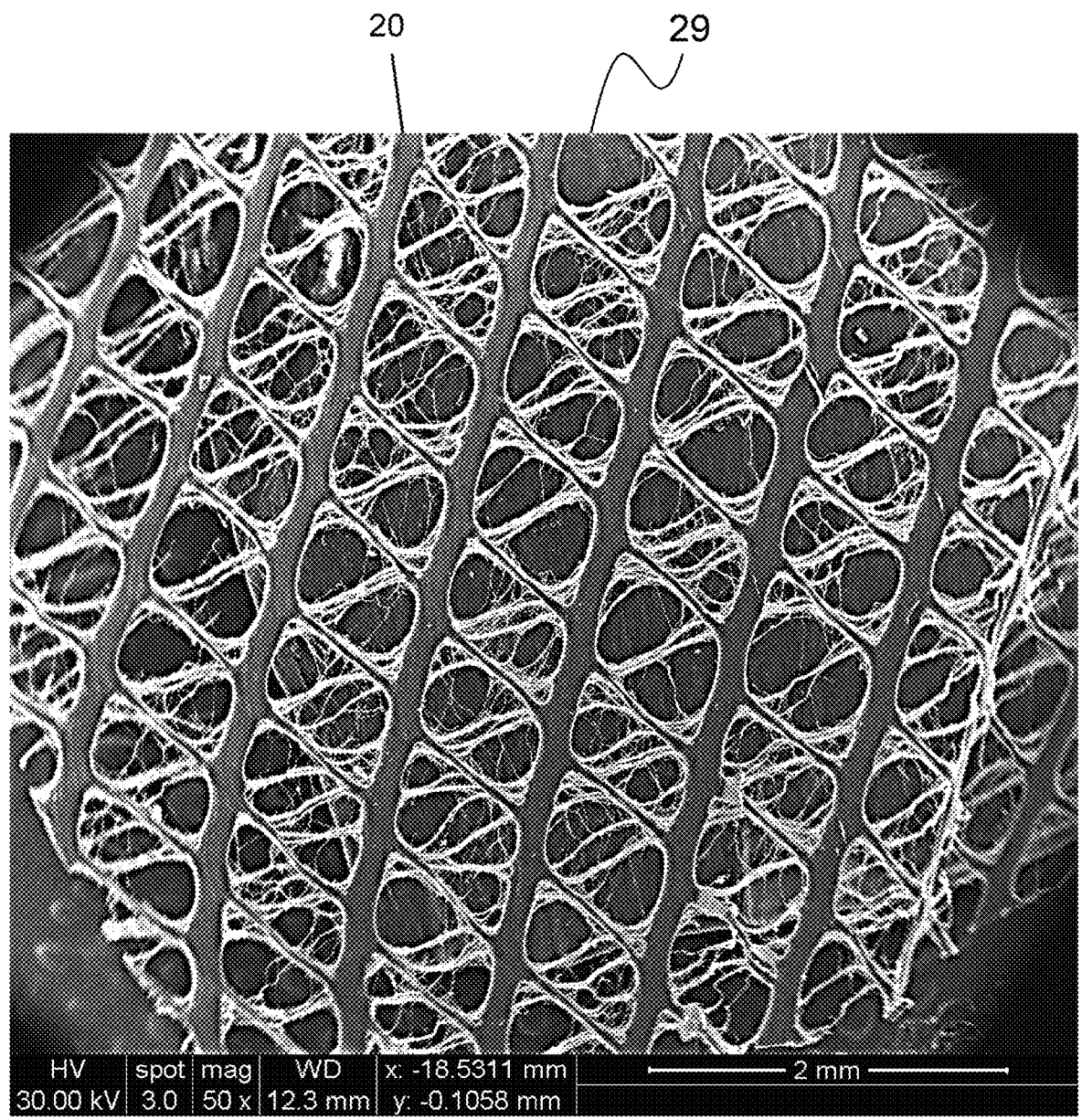
FIG. 11 is a scanning electron micrograph (SEM) representation of an amniotic membrane having pores between the amniotic membrane tissue.

As shown in FIG. 11, a representation of an amniotic membrane 20 comprises pores 29 between the amniotic membrane tissue. This porosity may be imbibed with an acellular amnion derived therapeutic composition. In addition, an amniotic membrane may be stretched in one or more directions to tensilize the tissue. A tensilized amniotic membrane may have a higher matrix tensile strength than an original un-tensilized amniotic membrane. In addition, a plurality of layers of amniotic membrane may be utilized to build strength in one or more directions.

Figure 12A:
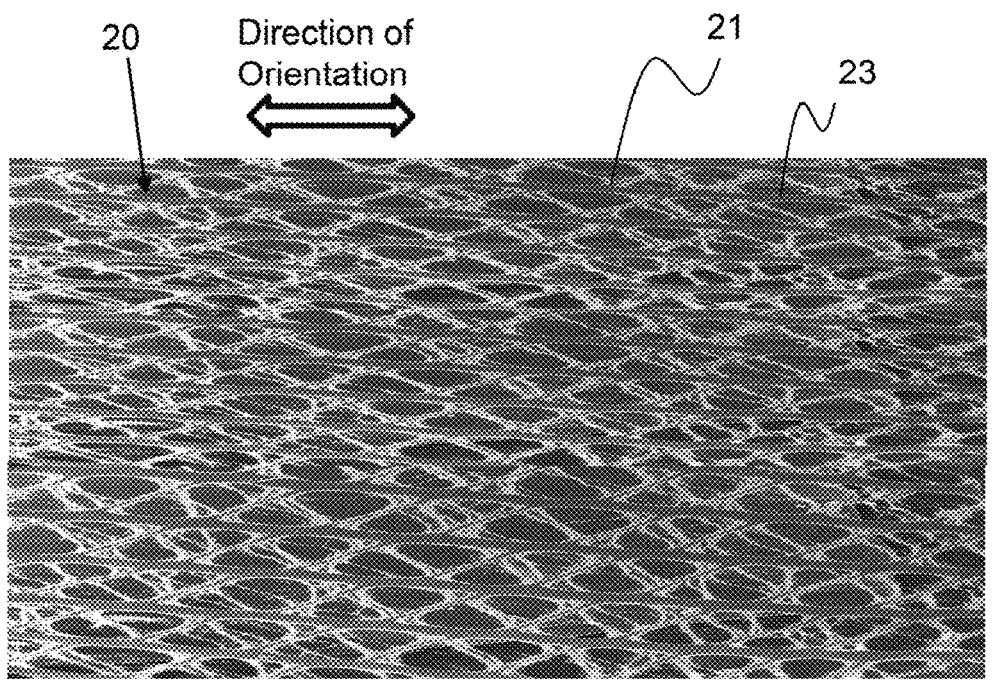
FIG. 12A is a representation of an exemplary tensilized amniotic membrane.

As shown in FIG. 12A, an amniotic membrane 20 has been stretched in one direction to form an elongated and more aligned amniotic tissue orientation. As shown in FIG. 12A, oriented tissue 23 is aligned horizontally and connecting tissue interconnects the oriented tissue. A tensilized amniotic membrane 21 may be stronger by unit weight in the oriented direction and may have a much higher elongation to break in the cross-oriented direction than a precursor amniotic membrane, before tensilizing. The tensilized amniotic membrane 21 may be stretched as much as 120%, 150%, 175%, or 200% of the original membrane length. The amniotic membrane may neck or narrow in the opposing direction of stretch. A stretched or tensilized amniotic membrane may be stretched over a long period of time to minimize tissue fracture. For example, an amniotic membrane may have a low load applied and may be stretched over a period of 10 minutes or more, 30 minutes or more, 1 hour or more, 6 hours or more, 1 day or more, 2 days more and any range between and including the durations provided. In addition, an amniotic membrane may be stretched while being hydrated and/or submerged in amniotic fluid or a plasticizing fluid. An amniotic membrane may be cross-linked after being stretched. The load applied to tensilize an amniotic membrane may be a portion of the maximum tensile load required to fracture the amniotic membrane at a rate of 10 mm/second for a 25.4 mm by 15.24 cm sample having a 50.8 mm gap. For example, a tensilizing load applied may be no more than about 80%, no more than about 60%, no more than about 50%, or no more than about 25% of the maximum tensile load.

Figure 12B:
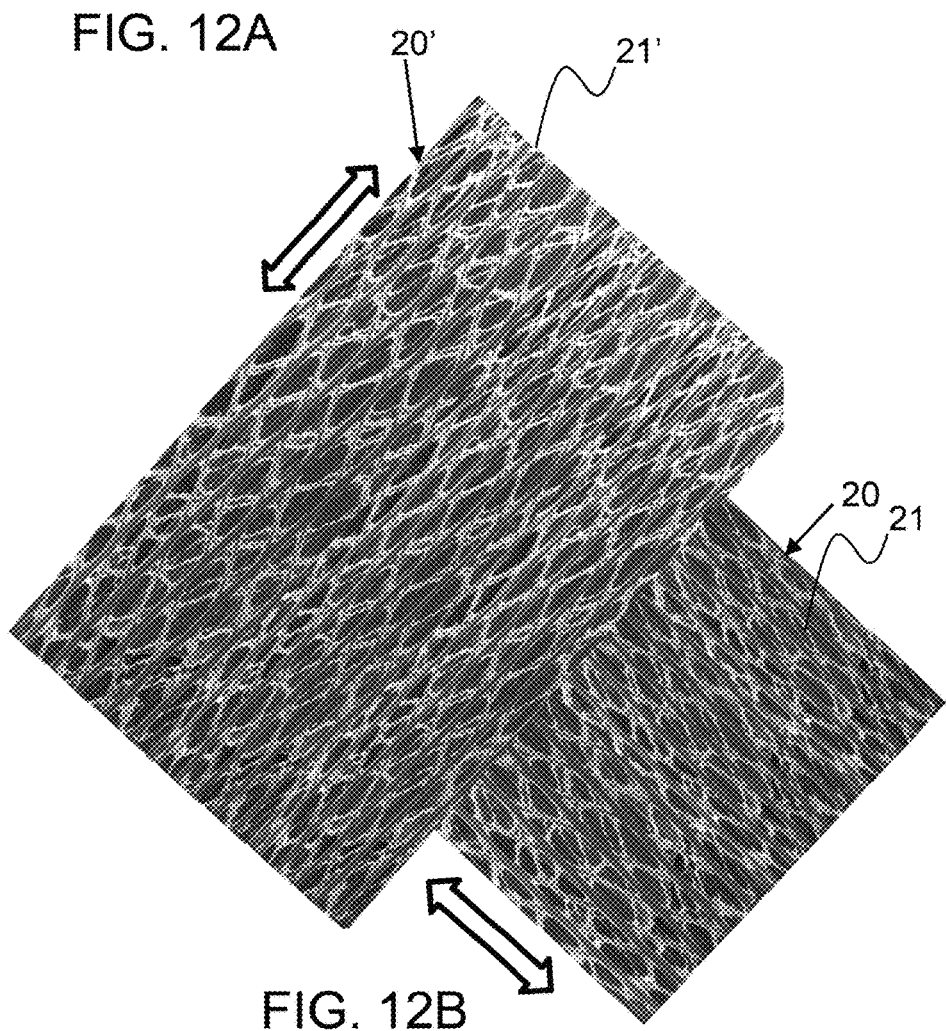
FIG. 12B is a representation of two exemplary tensilized amniotic membranes being layered together.

As shown in FIG. 12B, a first tensilized amniotic membrane 20 is configured at a 90 degree offset from a second amniotic membrane 20'. This orientation of layering may provide for a much stronger therapeutic composite. In an alternative embodiment, a plurality of layers of tensilized amniotic membrane may be aligned with the oriented tissue of a first layer being aligned with the oriented tissue of a second layer. A matrix component or a therapeutic composite, as described herein, may consist essentially of tensilized amniotic membrane.

Figure 13:
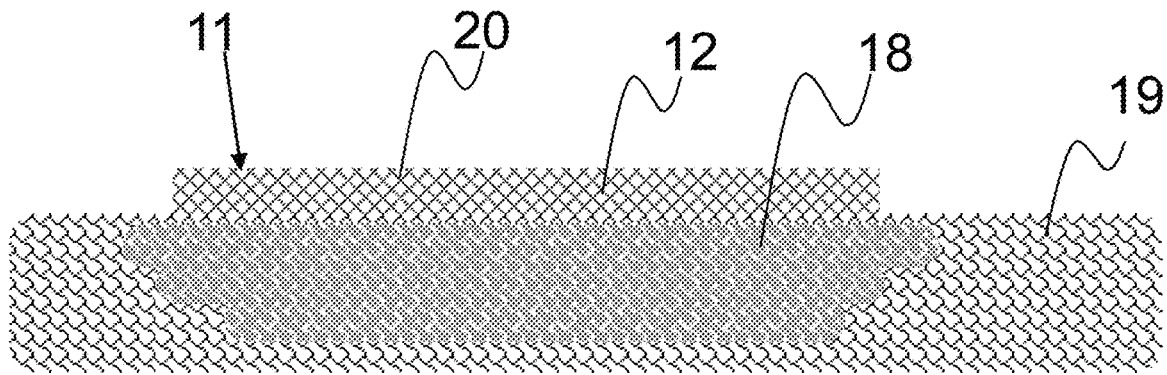
FIG. 13 shows a cross-sectional representation of an exemplary acellular amnion derived therapeutic composite comprising an amniotic membrane configured over a treatment location.

As shown in FIG. 13, an exemplary acellular amnion derived therapeutic composite 11 comprises an amniotic membrane 20 configured over a treatment location 18 in the tissue 19 of a subject. The matrix component 12 in this embodiment consists essentially of amniotic membrane 20.

Figure 14:
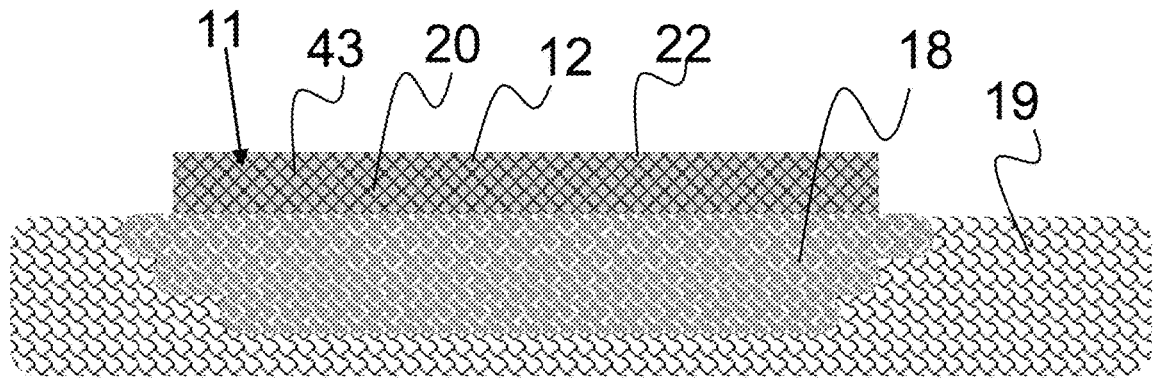
FIG. 14 shows a cross-sectional representation of an exemplary acellular amnion derived therapeutic composite comprising an amniotic membrane and fluid component configured over a treatment location.

As shown in FIG. 14, an exemplary acellular amnion derived therapeutic composite 11 comprises an amniotic membrane 20 and fluid component 14 configured over a treatment location 18. The fluid component 14 comprises micronized amniotic membrane particles 22 and amniotic fluid 43. Any suitable fluid carrier may be used to disperse the micronized amniotic membrane particles and/or amniotic fluid.

Figure 15:
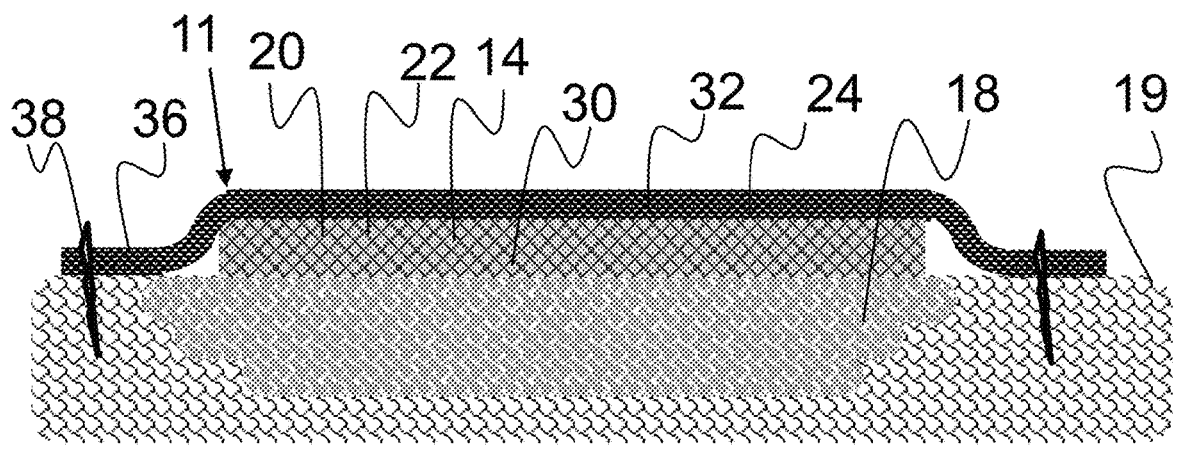
FIG. 15 shows a cross-sectional representation of an exemplary acellular amnion derived therapeutic composite configured over a treatment location wherein the therapeutic composite comprises an amniotic membrane imbibed with a fluid component and a cover layer configured there over.

As shown in FIG. 15, an exemplary acellular amnion derived therapeutic composite 11 is configured over a treatment location 18 wherein the therapeutic composite comprises an acellular amniotic membrane 20 imbibed with a fluid component 14 and a cover layer 24 is configured there over. The matrix component 12 comprises a first matrix layer 30 and a second matrix layer 32. The second matrix layer is configured over said first matrix layer and comprises an overhang portion 36 that extends outside of the first matrix layer. The second matrix layer is attached to the tissue 19 by an attachment component 38, such as a staple, glue and/or sutures, for example. A matrix component, or a layer of a matrix component, may be configured to extend beyond a treatment location, whereby an outer area of the matrix component can be affixed to tissue. A cover layer may fully cover a first or under layer of matrix component or may only cover a portion of a layer thereunder. A cover layer may be a net or mesh or strands that extend across and over an under-layer, for example.

Figure 16:
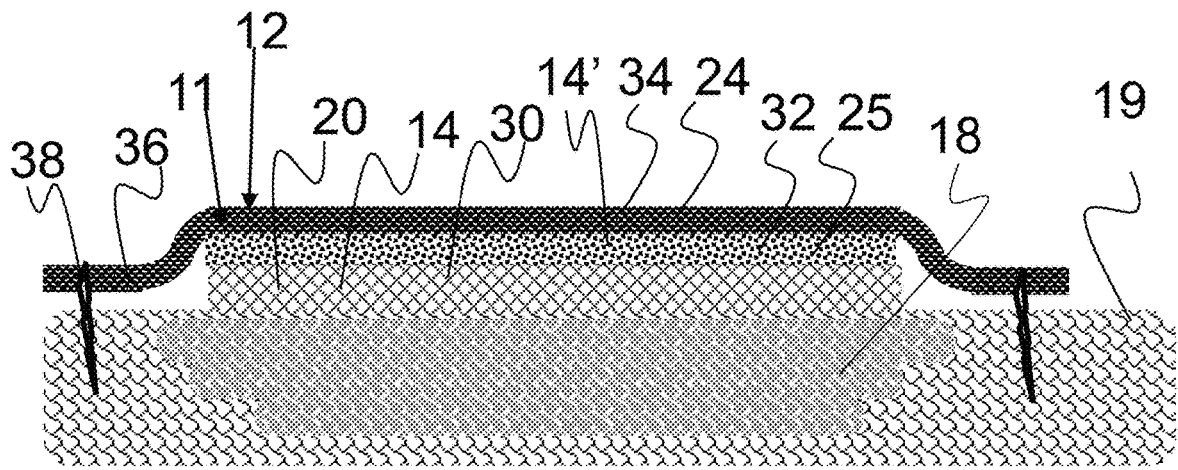
FIG. 16 shows a cross-sectional representation of an exemplary acellular amnion derived therapeutic composite configured over a treatment location wherein the therapeutic composite comprises a first matrix layer of amniotic membrane, a second matrix layer of a fluid component reservoir, and a third matrix layer that is a cover layer.

As shown in FIG. 16, an exemplary acellular amnion derived therapeutic composite 11 is configured over a treatment location 18. The acellular therapeutic composite 11 comprises a matrix component 12 comprising a first matrix layer 30 of amniotic membrane 20, a second matrix layer 32 of a fluid reservoir layer 25, and a third matrix layer 34 that is a cover layer 24. The fluid reservoir layer comprises a matrix having porosity containing a fluid component 14', as described herein. As shown, a first fluid component 14 is configured within the first matrix layer 30. It is to be noted that different compositions of a first and second fluid component may be configured in a matrix component 12.

Figure 17:
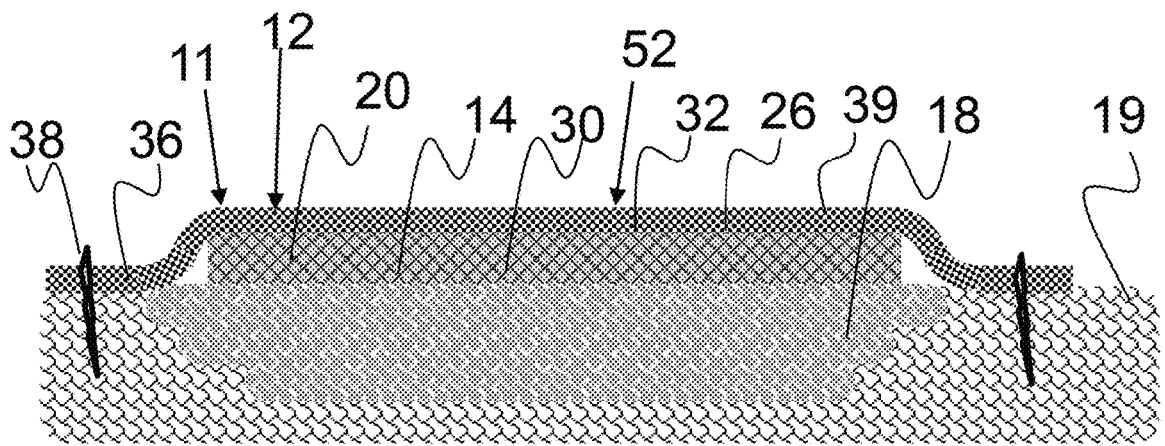
FIG. 17 shows a cross-sectional representation of an exemplary acellular amnion derived therapeutic composite configured over a treatment location wherein the therapeutic composite comprises a first matrix layer of amniotic membrane imbibed with fluid component and a second matrix layer that is a support layer comprising bioresorbable material.

As shown in FIG. 17, an acellular amnion derived therapeutic composite 11 is configured over a treatment location 18 wherein the matrix component 12 comprises a first matrix layer 30 of amniotic membrane 20 imbibed with fluid component 14 and a second matrix layer 32 that is a support layer 39 comprising bioresorbable material 26. The support layer may be substantially impermeable to the fluid component configured in the first matrix component that is proximate a treatment location. In addition, an outer surface 52 of a matrix component 12, or the surface facing away a treatment location, may be hydrophobic to reduce fluid ingress into the therapeutic composite. Bodily fluid ingress into a therapeutic composite may dilute a fluid component comprised therein.

Figure 18:
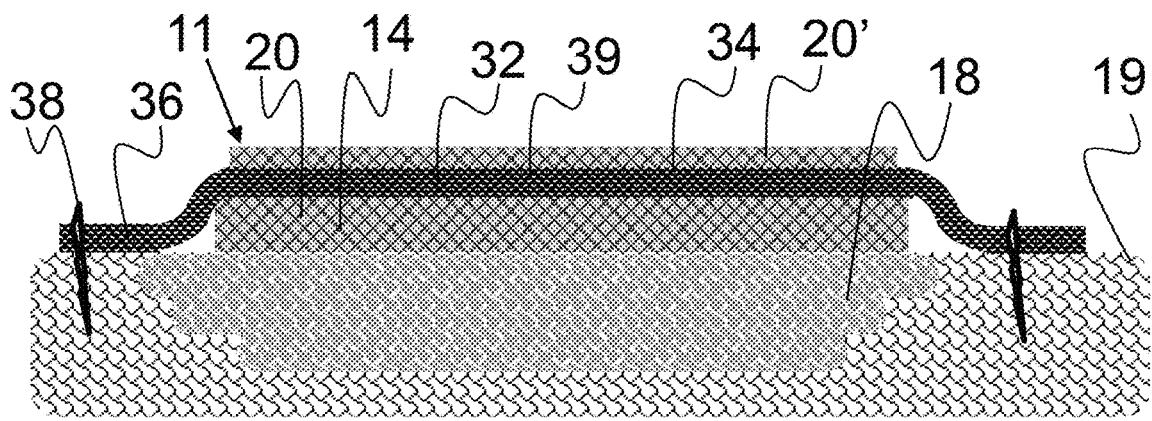
FIG. 18 shows a cross-sectional representation of an exemplary acellular amnion derived therapeutic composite configured over a treatment location wherein the therapeutic composite comprises a first matrix layer of amniotic membrane imbibed with fluid component, a second matrix layer that is a support layer and a third matrix layer that comprises amniotic membrane.

As shown in FIG. 18, an exemplary acellular amnion derived therapeutic composite 11 is configured over a treatment location 18 wherein the matrix component 12 comprises a first matrix layer 30 of amniotic membrane 20 imbibed with fluid component 14, a second matrix layer 32 that is a support layer 39 and a third matrix layer 34 that comprises amniotic membrane 20. A support layer is configured between amniotic membranes in this embodiment. As described herein, a matrix component may be provided with multiple layers attached and ready for orientation on a treatment location, or a plurality of matrix components may be applied, one after another, during the treatment procedure.

Figure 19:
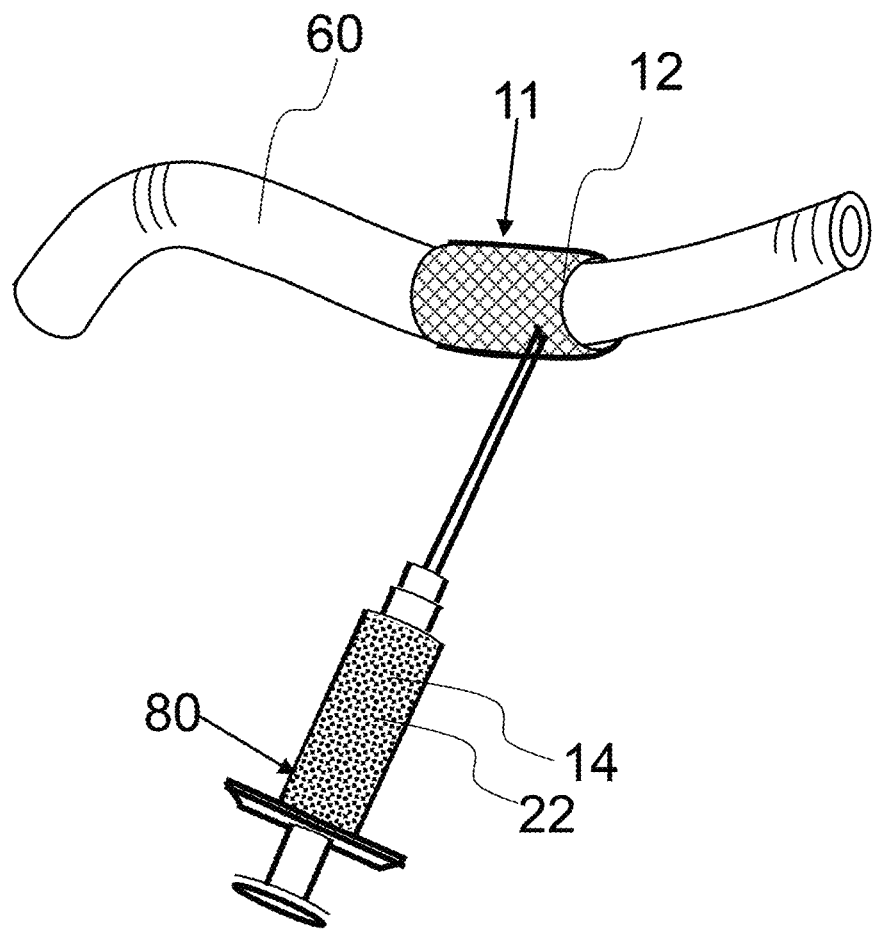
FIG. 19 shows an exemplary therapeutic composite configured around a ureter and a fluid component being injected therein.

As shown in FIG. 19, an exemplary acellular amnion derived therapeutic composite 11 is configured around a ureter and a fluid component 14 is being injected therein. This type of procedure may reduce and/or eliminate strictures. A matrix component may be a sheet of material having a substantially planar top and bottom surface and substantially uniform thickness therebetween. A sheet of matrix composite may be supple and may be configured around a cylindrical treatment location, such as a portion of the urinary or digestive system. In another embodiment, a matrix component sheet is applied externally over a treatment location in a patient's dermal tissue. It is to be understood that a composition comprising viable cells may be injected into or otherwise placed into contact with an acellular amnion derived therapeutic composite, as described herein. For example, the syringe 80 shown in FIG. 19 may comprise live viable stem cells that are injected into an exemplary acellular amnion derived therapeutic composite 11. The stem cells may be any suitable type of stem cells.

Figure 20:
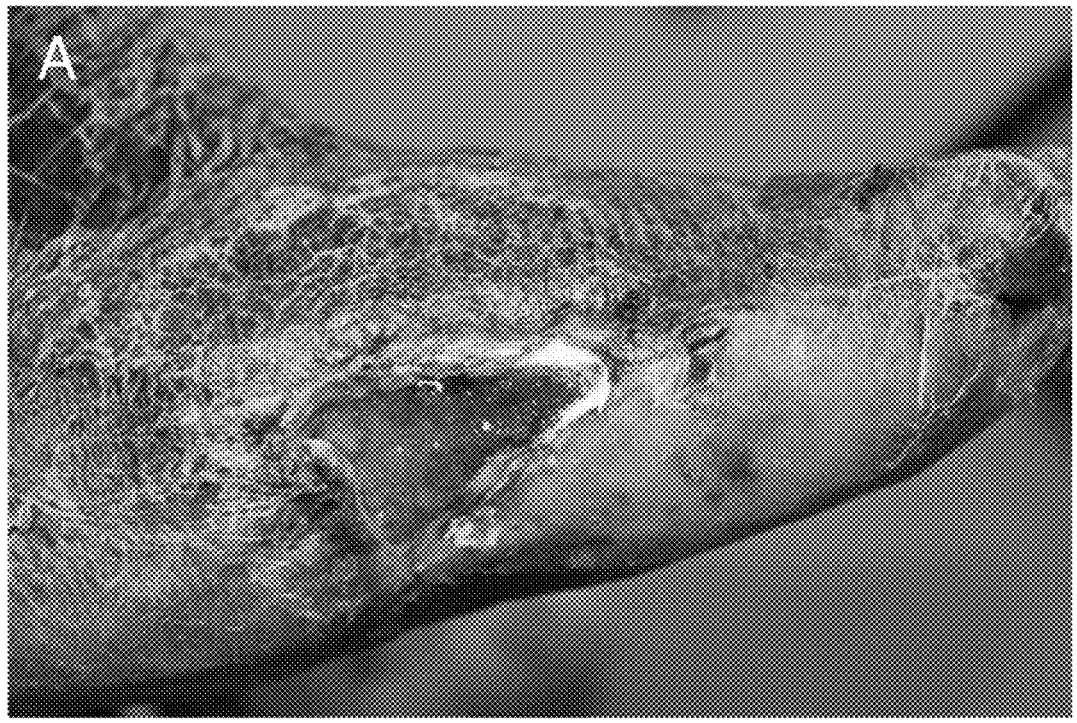
FIG. 20 shows a picture of a wound on a diabetic person's foot prior to treatment.

As shown in FIG. 20, a wound on a diabetic person's foot has a length of approximately 11 mm and width of approximately 7 mm. An acellular amnion derived therapeutic composite of amniotic membrane may be placed over the wound and a fluid component comprising micronized amniotic membrane and a concentrated amniotic fluid may be applied topically. Stem cells derived from the patient's stromal vascular fraction may be applied to the treatment location as well.

Figure 21:
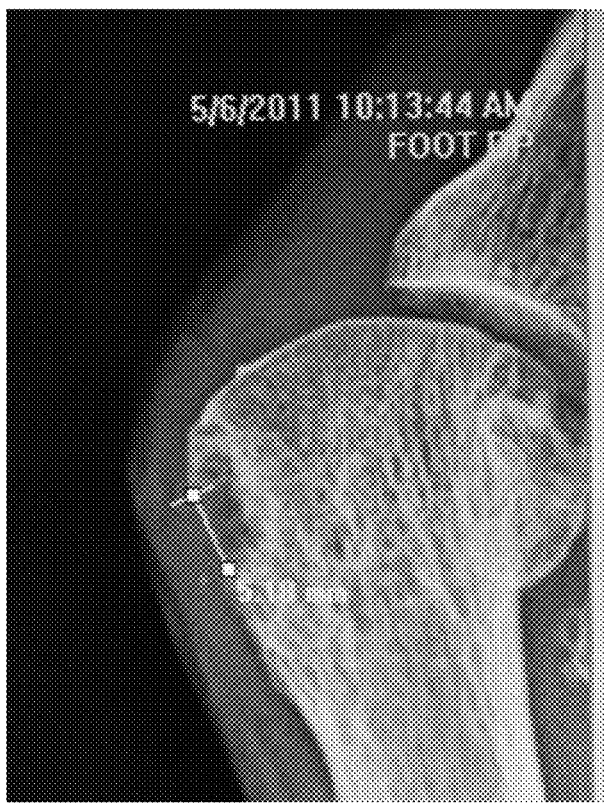
FIG. 21 shows an x-ray of an osteochondral defect in an ankle, prior to treatment.

As shown in FIG. 21, a patient has an osteochondral defect in an ankle, with some bone degradation. An acellular amnion derived therapeutic composite may be applied over the defect and an acellular amnion derived therapeutic fluid component may then be applied to the treatment site.

Figure 22:
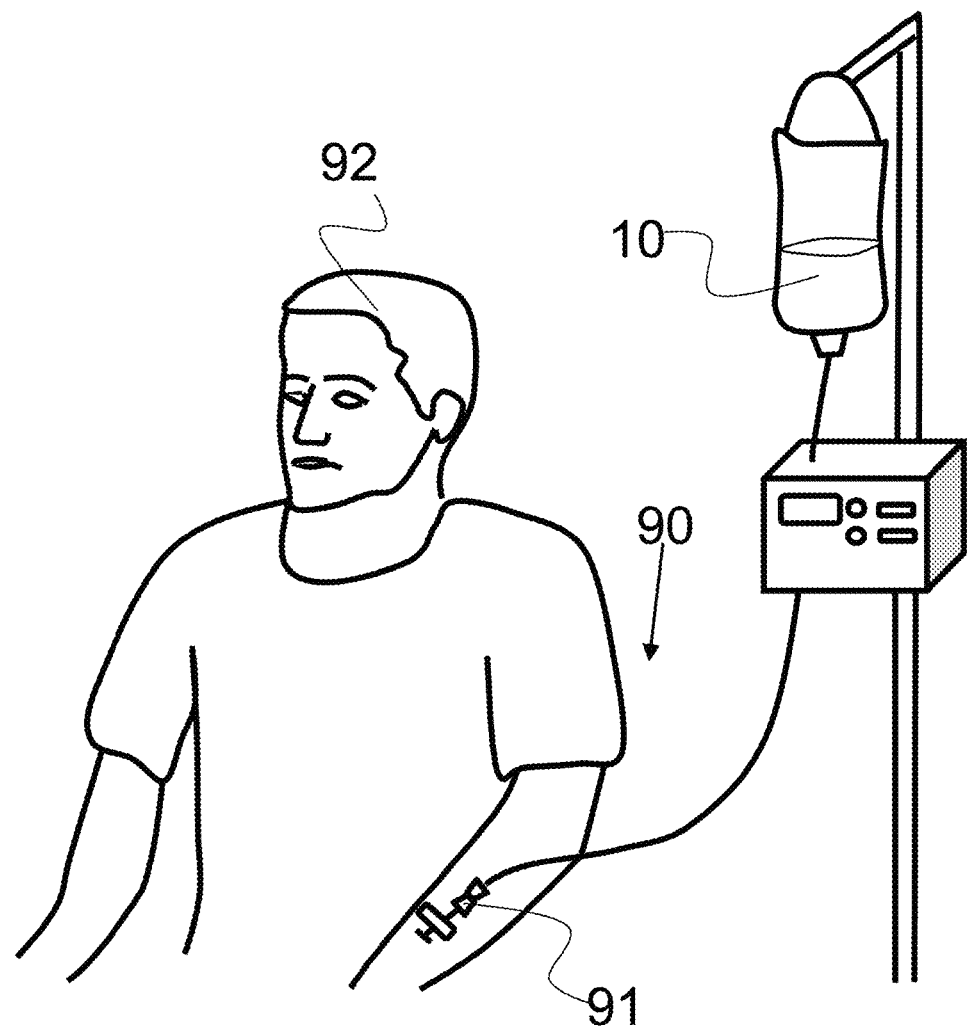
FIG. 22 shows an acellular amniotic derived composition being administered intravenously through a catheter.

As shown in FIG. 22, a patient 92 is receiving an intravenous treatment 90 of an acellular amnion derived composition 10, as described herein. The acellular amnion derived composition 10 is being introduced intravenously through a catheter 91.

Figure 23:
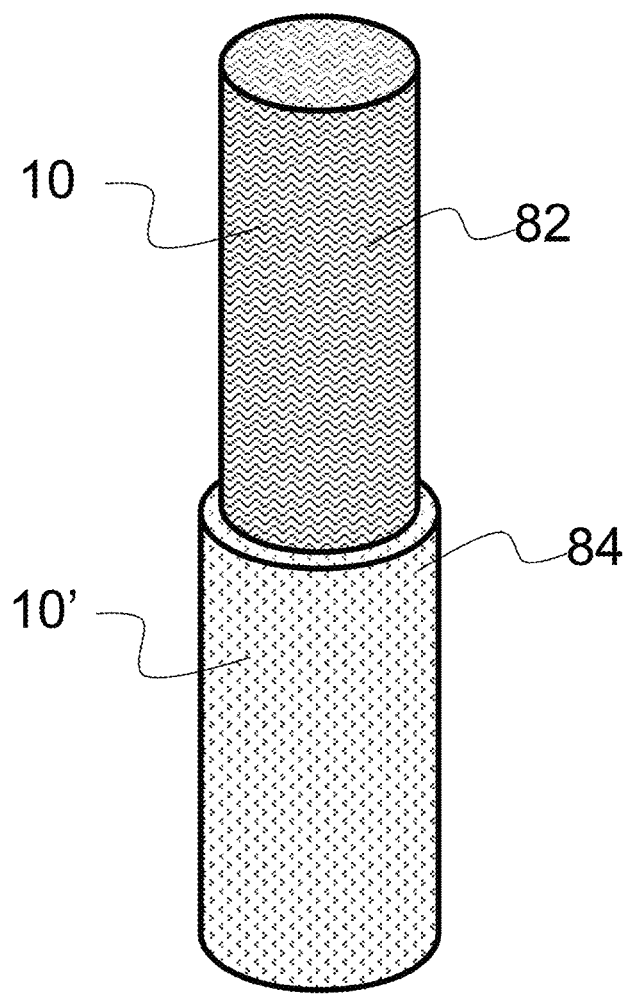
FIG. 23 shows a stent having an acellular amniotic derived composition configured thereon.

As shown in FIG. 23, a stent 82 having a stent covering 84 on a portion of the stent comprises an acellular amnion derived composition 10. As described herein, an acellular amnion derived composition may be coated onto a stent 82, such as a metal stent, or coated onto or imbibed into a stent covering, such as an expanded fluoropolymer material. Expanded PTFE is often used in covered stent applications and an acellular amnion derived composition may be coated onto or imbibed into the porosity, or pores of the expanded PTFE. In another embodiment, an amniotic membrane is configured as a stent covering and an acellular amnion derived composition may be combined with the amniotic membrane to form a stent covering.

Example 1: Lubricating Composition Preparation (AT21-001)

Figure 25:
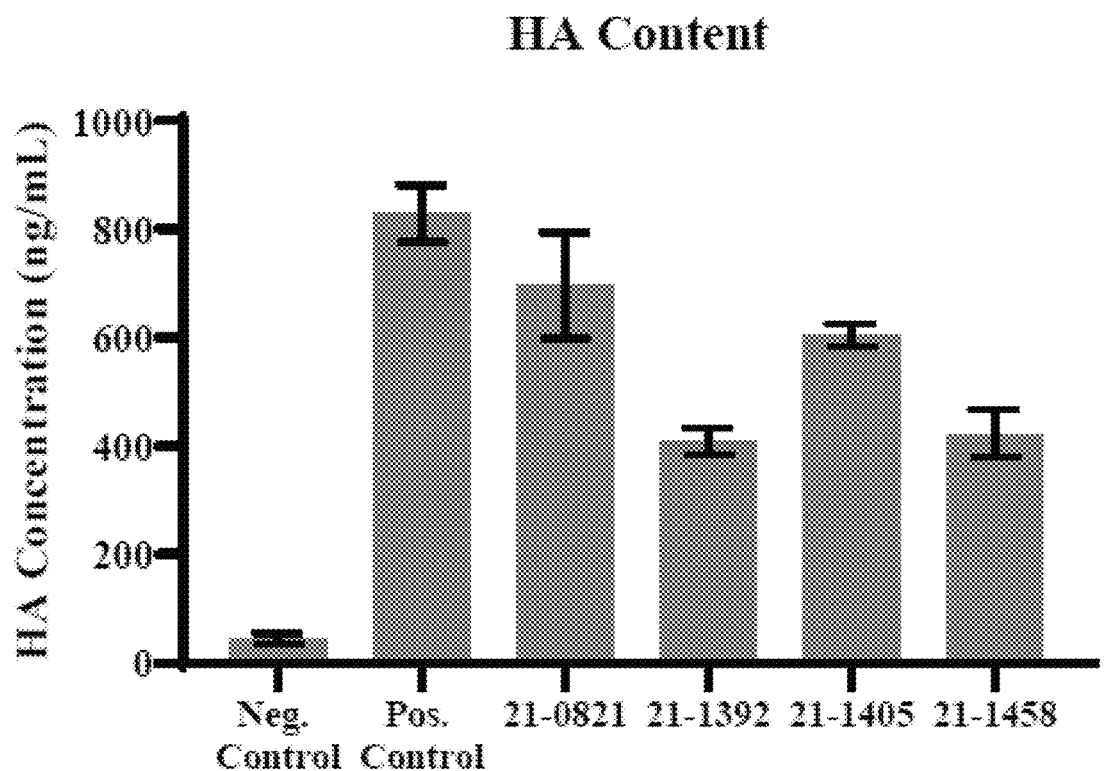
FIG. 25 shows a graph of the Hyaluronic Acid (HA) content.
Figure 26:
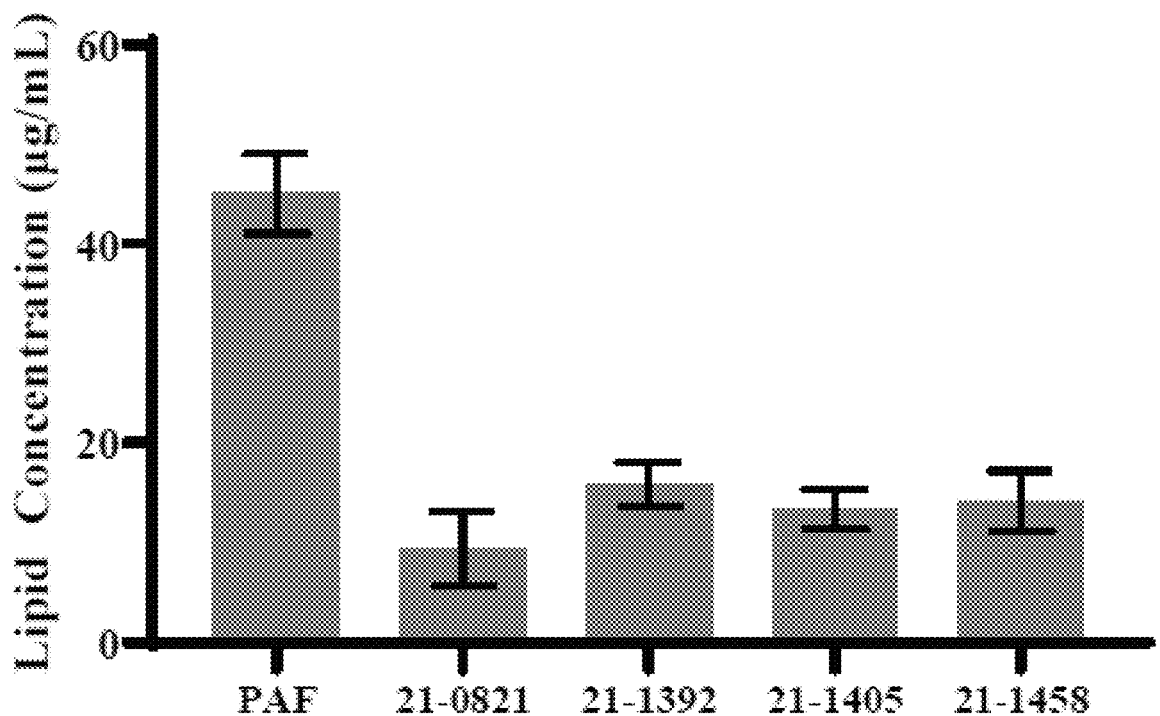
FIG. 26 shows a graph of the phospholipid content.

A lubricating composition (AT21-001) was produced from amniotic fluid. The amniotic fluid was first filtered with a calculi filter, to produce a prefiltered amniotic fluid with particles removed that are 200 microns or larger, or in some cases 150 microns or larger, such as bodily tissue, baby lanugo or hair. The pre-filtered amniotic fluid was then spun to separate out the amniotic fluid from and the insoluble components that were collected as a pellet. The spun amniotic fluid was then filtered through a 20 micron filter, or filter configured to remove particles greater than 20 microns, to produce a filtered amniotic fluid. This filtered amniotic fluid was then mixed with a 10% DMSO solution, the pellet was also mixed in to create the lubricating mixture. The lubricating mixture was then cryogenically frozen at a controlled rate to prevent crystallization to a temperature −90 C or below. The cryogenically frozen lubricating mixture was then irradiated to produce a sterile lubricating mixture. The sterile lubricating mixture was then thawed to produce the lubrication composition AT21-001. This lubricating composition, was used to make four lots that were tested for various component concentrations, lots 21-0821, lot 21-1392, lot 21-1405 and lot 21-1458, as seen in FIGS. 25 and 26.

Example 2: Lubricating Composition Preparation (AT21-002)

A lubricating composition (AT21-002) was produced from amniotic fluid. The amniotic fluid was first filtered with a calculi filter, to produce a prefiltered amniotic fluid with particles removed that are 200 microns or larger, or in some cases 150 microns or larger, such as bodily tissue, baby lanugo or hair. The pre-filtered amniotic fluid was then spun to separate out the amniotic fluid from and the insoluble components that were collected as a pellet. The spun amniotic fluid was then filtered through a 20 micron filter, or filter configured to remove particles greater than 20 microns, to produce a filtered amniotic fluid. This filtered amniotic fluid was then mixed with a 10% DMSO solution, to create the lubricating mixture. The lubricating mixture was then cryogenically frozen at a controlled rate to prevent crystallization to a temperature −90 C or below. The cryogenically frozen lubricating mixture was then irradiated to produce a sterile lubricating mixture. The sterile lubricating mixture was then thawed to produce the lubrication composition AT21-002.

Example 3: Lubricating Composition Preparation (AT21-003)

A lubricating composition (AT21-003) was produced from amniotic fluid. The amniotic fluid was first filtered with a calculi filter, to produce a prefiltered amniotic fluid with particles removed that are 200 microns or larger, or in some cases 150 microns or larger, such as bodily tissue, baby lanugo or hair. The prefiltered amniotic fluid was then filtered through a 20 micron filter, or filter configured to remove particles greater than 20 microns, to produce a filtered amniotic fluid. This filtered amniotic fluid was then mixed with a 10% DMSO solution, to create the lubricating mixture. The lubricating mixture was then cryogenically frozen at a controlled rate to prevent crystallization to a temperature −90 C or below. The cryogenically frozen lubricating mixture was then irradiated to produce a sterile lubricating mixture. The sterile lubricating mixture was then thawed to produce the lubrication composition AT21-003.

Example 4: Tendon Friction Test

Test performed by: Bioengineering Devices Lab (Flagstaff, AZ)

Figure 24:
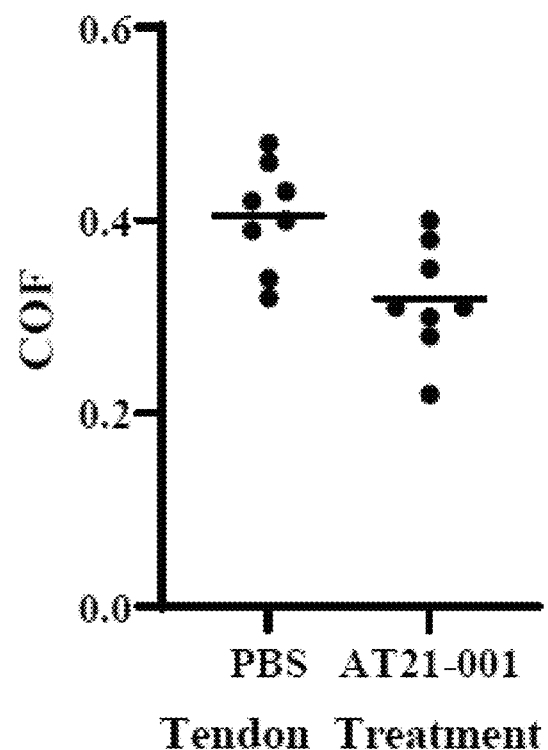
FIG. 24 shows a graph of coefficient of friction (COF) of a human tendon comparing saline to a therapeutic composition as described herein.

A therapeutic composition, AT21-001 a lubricating composition, may act to reduce friction and gliding resistance in tendons. A Human gracilis tendon was treated with an amnion derived therapeutic composition (AT21-001) and demonstrated a lower coefficient of friction (COF) compared to tendon treated with phosphate buffered saline (PBS), as shown in FIG. 24. Donated human gracilis tendon (GR-11, Pinnacle Transplant Technologies; Phoenix, AZ) was handled and thawed according to the manufacturer instructions for use. Tendons were trimmed to expose the sheath and soaked in either PBS or AT21-001 for 12 hours at 4° C. prior to testing. The apparent lubricities of the tendon samples were measured using a DHR-2 hybrid rheometer with a catheter fixed to a force plate. The catheter was guided via a low friction bearing to a sample support wheel affixed with the tendon sample. The tendon sample was then submerged in 5 ml of either PBS or AT21-001. The DHR-2 measured frictional force as the upper geometry pulled 5 cm of the catheter across each sample.

Frictional and normal force at the tendon were used to calculate the coefficient of friction. Coefficients of Friction of tendons treated with either AT21-001 or PBS. Data represents a total of two separate experiments with four replicates each run (data points). Mean COF for PBS control was 0.4050 compared to AT21-001 treatment mean COF of 0.3188 (horizontal lines). The difference in COF between the AT21-001 treatment and control were significant (P=0.0084) in an unpaired two-tailed t-test (P<0.05).

Results of the lubricity testing demonstrated that AT21-001 treatment was sufficient to reduce the frictional force measured on the human tendon when compared to treatment in control saline. Duplicate experiments were conducted, and each run was composed of four replicates. The data were combined to determine an experimental mean COF for PBS and AT21-001 (FIG. 3). The difference in mean COFs between the two treatments was significant in an unpaired, two-tailed t-test (P=0.0084, P<0.05).

The ability of a therapeutic composition, as describe herein to act as a lubricant and reduce the gliding friction at the tendon surface is conferred by the hyaluronic acid, proteoglycans, and phospholipids inherent to amniotic fluid. Initial product characterization data is included, below, including the identification and quantification of key molecules in AT21-001 which contribute to the primary mechanism of action.

Figure 30:
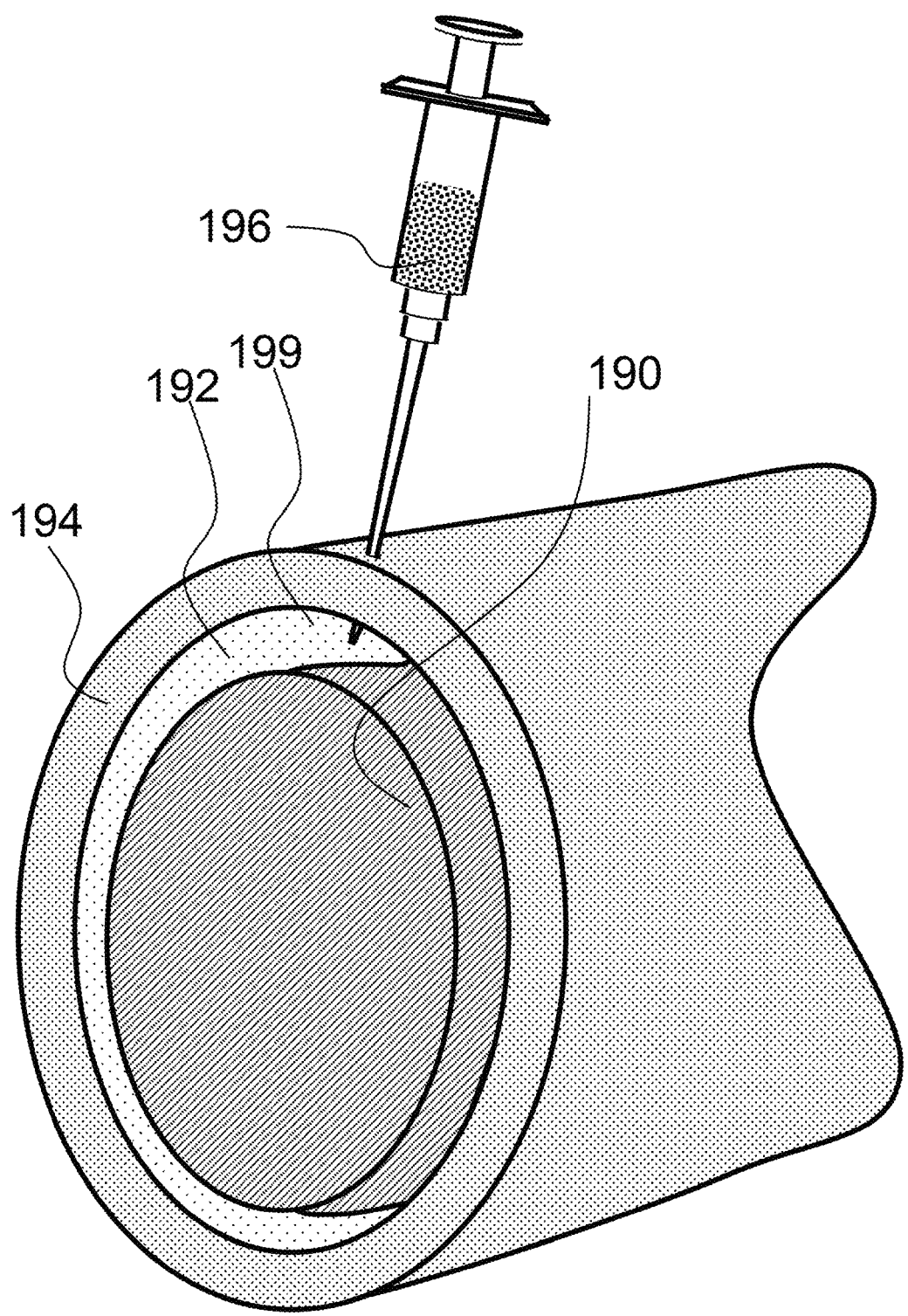
FIG. 30 shows a perspective view of a tendon and tendon sheath with an amnion derived therapeutic composition configured within the sheath for lubricating the movement of the tendon therein.

As shown in FIG. 30, a therapeutic composition 10, a lubricating composition 196, such as a lubrication fluid 199 may be injected through the tendon sheath 194 and into the interstitial space 192 between the tendon 190 and the tendon sheath 194. As shown, the syringe has a needle that punctures through the tendon sheath to inject the lubricating fluid 199 into the interstitial space 192. An exemplary lubricating composition is a lubricating fluid that flows and can be injected through a syringe as shown.

Hyaluronic Acid Content—FIG. 25

With reference to FIG. 25, Hyaluronic Acid (HA) is a high molecular weight anionic polysaccharide composed of repeating disaccharides. The viscoelastic properties of hyaluronic acid are dependent on its high molecular weight and semi-flexible chain; whereby the large HA polymers increase in volume faster than in mass. The concentration of hyaluronic acid in a therapeutic composition was measured using a competitive ELISA protocol (K-1200, Echelon; Salt Lake City, UT). Assay controls included a blank (negative) control of product solvent and water and unprocessed amniotic fluid (positive control). Four developmental lots of therapeutic composition and control samples were tested according to the manufacturer's directions and plated in five replicates each.

Hyaluronic acid concentrations were interpolated from a standard curve generated during the assay hyaluronic acid concentrations measured in the product lots were 696.5 ng/mL (lot number 21-0821), 409.2 ng/mL (21-1392), 604.9 ng/mL (21-1405), and 423.2 ng/mL (21-1458). Unprocessed amniotic fluid from a single donor, included as a positive control, contained 828.4 ng/mL HA. Product solvent tested as a negative control showed minimal background, see FIG. 25. An exemplary therapeutic composition and particularly a lubricating fluid as described herein may have a hyaluronic acid concentration of about 200 ng/ml or more, about 300 ng/ml or more, about 400 ng/ml or more, about 600 ng/ml or more and any range between and including the hyaluronic acid concentrations provided. A higher hyaluronic acid concentration may aid in providing low friction or longer lasting lubricating effects, particularly between a tendon and tendon sheath.

Phospholipid Content See FIG. 26

Total choline-containing phospholipids were measured in a therapeutic composition using a commercially available colorimetric kit (ab234050, Abcam; Waltham, MA). PAF (1-alkyl-2-acetoyl-sn-glycero-3-phosphocholine) from heart pericardium (Avanti; Alabaster, AL) was prepared at a concentration of 60 μM (46 μg/mL) and included as a positive control (PAF).

Figure 27:
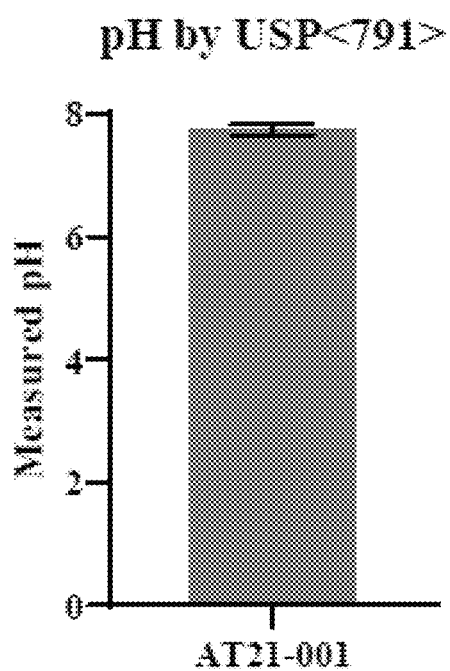
FIG. 27 shows a graph of the pH of an amnion derived therapeutic composition.
Figure 28:
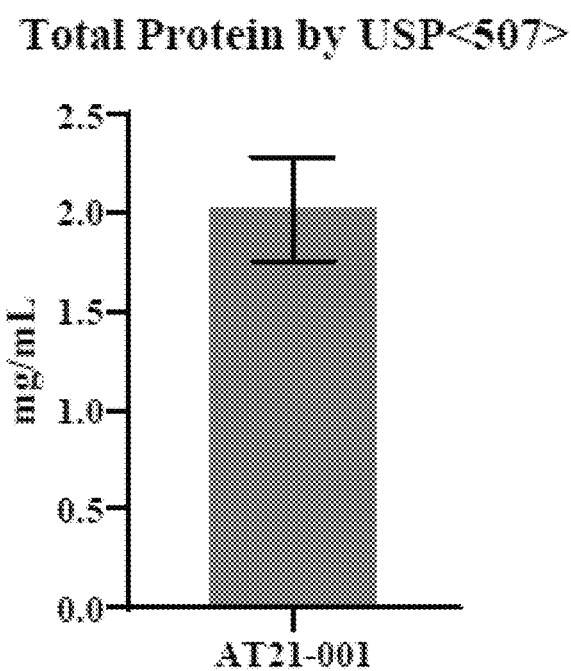
FIG. 28 shows the total protein content of an amnion derived therapeutic composition.

Total choline-containing lipids were measured in four developmental lots of a therapeutic composition, and more particularly; the resulting concentrations were: 9.4 μg/mL (lot number 21-0821), 15.8 μg/mL (21-1392), 13.3 μg/mL (21-1405), and 14.2 μg/mL (21-1458). Calculated concentration of positive control PAF preparation was as expected (See FIG. 26). Therefore the total lipid concentration of a therapeutic composition, or lubricating composition AT21-001 as described herein, may be about 8 μg/mL or more, about 10 μg/mL or more, about 12 μg/mL or more, about 14 μg/mL or more and any range between and including the lipid concentrations provided.

pH and Total Protein Content—FIGS. 27 and 28

The pH and total protein of AT21-001 were measured using compendial methods, USP<791> and USP<507> method II, respectively. Mean pH of AT21-001 is 7.7 with a standard deviation of 0.09 (FIG. 27). Mean protein concentration is 2.02 mg/ml with a standard deviation of 0.26 mg/ml (FIG. 28). USP <791> refers to the standardized test method for pH measurements used in the pharmaceutical, food and beverage, patient care, and dietary supplement industry.

Figure 29:
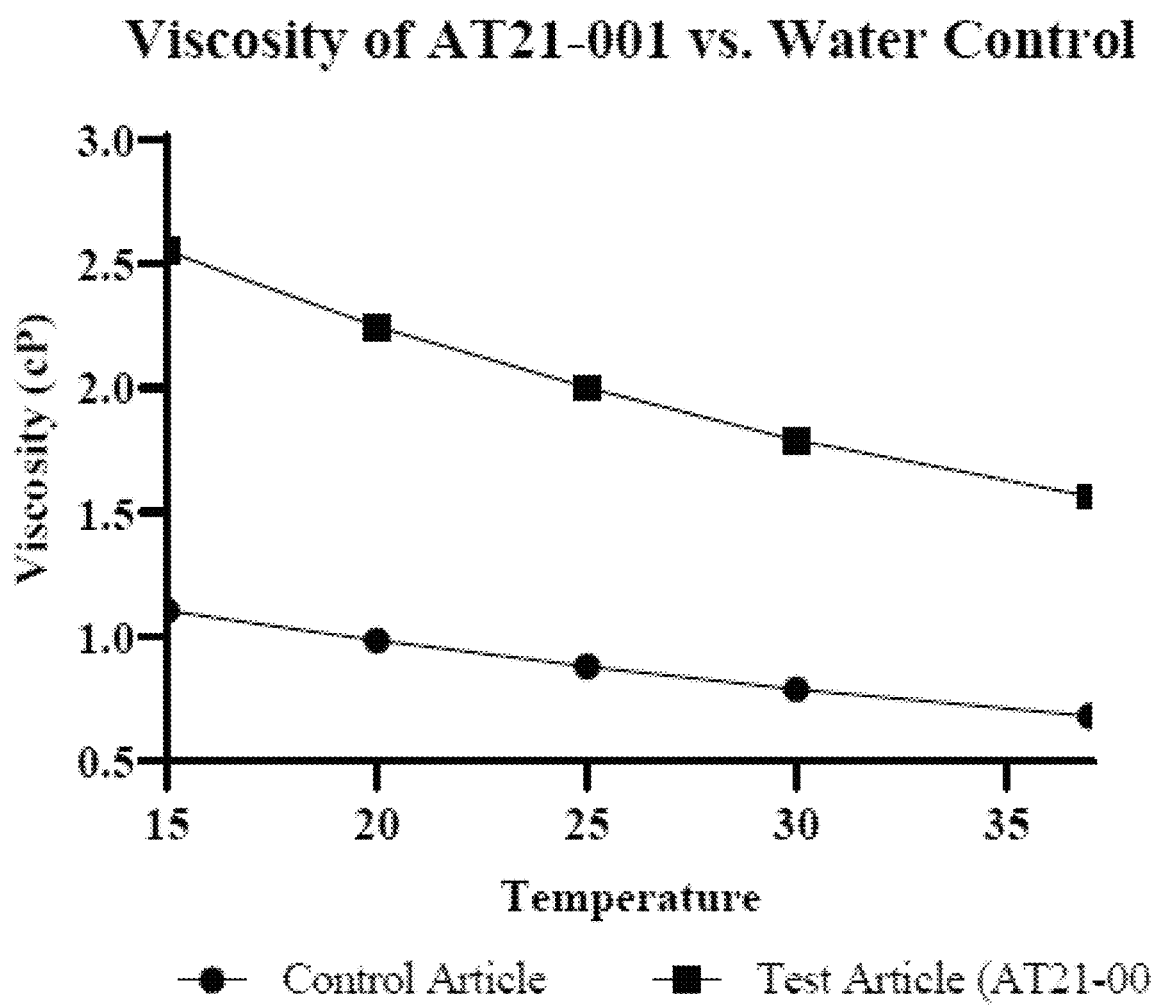
FIG. 29 shows a graph of viscosity of an amnion derived therapeutic composition versus water as a function of temperature.

Rheological Characterization—FIG. 29

The viscosity of AT21-001 was measured with a DHR-2 rotational rheometer with cone and plate geometry (40 mm diameter and 2° stainless steel cone). Samples of AT21-001 were tested at varying shear rates (50 s-1 to 500 s-1) and temperatures (20° C. to 37° C.). AT21-001 exhibited Newtonian fluid behavior across the temperature range tested. Some shear-thinning behavior was noted at the lowest shear rates; however, the product exhibited Newtonian fluid behavior between 300 s-1 and 500 s-1. This data suggests that AT21-001 is higher in viscosity than water alone at multiple temperatures including physiological temperatures (FIG. 29). At 20° C. the viscosity of the therapeutic composition or lubricating composition or fluid was about 2.3 cP.

Definitions

An acellular amnion derived composition is a material derived from amnion material, including amniotic membrane and amniotic fluid, but contains essentially no live amniotic cells. In an exemplary embodiment, an amnion derived acellular composition comprises no live or active amniotic derived cells including amniotic fluid and amniotic membrane cells. In yet another embodiment, an acellular amnion derived therapeutic composition comprises essentially no intact amniotic derived cells. As described herein, during the micronizing of the amniotic membrane, cells may be fractured leaving cell fragments and essentially no intact cells.

An acellular material, as used herein, is defined as a material having essentially no viable cells wherein no more than 1% of the total number of cells in the material are viable. In an exemplary embodiment, an acellular composition contains no viable cells. In an exemplary embodiment, an acellular composition is essentially cell free. Essentially cell free, as used herein, is defined as a composition that contains essentially no intact cells, or no more than five percent, no more than three percent, no more than two percent, or no more than one percent of an original intact cell concentration, or no more than about 750,000 intact cells per ml of material, no more than about 450,000 intact cells per ml of material, no more than about 300,000 intact cells per ml of material, or no more than about 150,000 intact cells per ml of material. An essentially cell free material may contain cell fragments that have been destroyed through cryo-fracturing, for example.

Micronized placental tissue particles, as used herein, is defined as particles derived from placenta including amniotic membrane (amnion), chorion, Wharton's Jelly, umbilical cord, and the like. Amniotic membrane particles may be preferred for therapeutics effectiveness. Placental tissue may be micronized to have an average particle size of no more than about 1000 um, and preferably no more than about 100 um, and may have an average particle size of no more than about 75 um, no more than about 50 um, no more than about 25 um, no more than about 10 um and any range between and including the average particle sizes provided. Particle size may be measured by analysis of scanning electron micrographs. Micronized placental tissue particles may be formed through any suitable method including, but not limited to, cryogenic fracturing, application of heat and pressure, sonication and/or enzyme digestion.

Amniotic fluid may be decellularized to remove a portion of the cells through centrifugation, for example. A decellularized amniotic fluid may be an essentially cell free amniotic fluid obtained through centrifugation, filtration, or other process to remove essentially all of the cells and/or cell debris and may contain essentially no intact cells, or no more than about five percent, no more than three percent, no more than two percent, or no more than one percent of an original intact cell concentration, or no more than about 750,000 intact cells per ml of material, no more than about 450,000 intact cells per ml of material, no more than about 300,000 intact cells per ml of material or no more than about 150,000 intact cells per ml of material.

An amniotic cell, as used herein is a cell derived from amniotic fluid or amniotic membrane.

An intact cell, as used herein, is a cell that is viable or non-viable and retains an original shape and has not been ruptured or split into two or more pieces.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A method of lubricating bodily tissue comprising:
   a) producing a lubricating composition comprising:
      i) providing an amniotic fluid comprising hyaluronic acid;
      ii) filtering the amniotic fluid to remove particles and wherein the lubricating composition has no particles greater than 20 μm in size;
      iii) providing a carrier fluid comprising:
         dimethyl sulfoxide (DMSO) in a concentration of at least 3% and no more than 20%;
      iv) combining the amniotic fluid and the carrier fluid to produce said lubricating composition;
      wherein carrier fluid is present in a concentration of no more than 60% by weight of the lubricating composition;
      wherein the lubricating composition is essentially free of any viable amniotic fluid cells;
      wherein the lubricating composition has a hyaluronic acid concentration of 200 ng/ml of the lubricating composition;
   b) irradiating the lubricating composition;
      wherein the lubricating composition is irradiated to sterilize the lubricating composition and wherein the lubricating composition is sterile to $10^{-6}$; and
   c) inserting the lubricating composition into said bodily tissue to lubricate the bodily tissue;
      wherein the bodily tissue is a tendon and wherein the lubricating composition is injected into an interstitial space between said tendon and a tendon sheath.

2. The method of claim 1, wherein carrier fluid comprises dimethyl sulfoxide (DMSO) in a concentration of at least 3% and no more than 10%.

3. The method of claim 1, wherein the viscosity of the lubricating composition is 1.2 cP to 3.0 cP at 20° C.

4. The method of claim 1, wherein the viscosity of the lubricating composition is 1.4 cP to 2.5 cP at 20° C.

5. The method of claim 1, wherein the amniotic fluid contains at least one proteins, cytokines, or growth factors selected from the group consisting of: bFGF, EGF, FGF-7, IGF-1, IL-4, IL-10, PDGF-AA, PDGF-BB, PDGF-AB, Pentraxin 3, TGFa, TGFP1, TiMP-1, TIMP-2, VEGF, and S100A8.

6. The method of claim 5, wherein the protein concentration is between 1.5 mg/ml and 2.5 mg/ml.

7. The method of claim 5, wherein the protein concentration is between 1.75 mg/ml and 2.25 mg/ml.

8. The method of claim 5, wherein the concentration of lipids in the lubricating composition is 10 μg/mL or more.

* * * * *